US012090192B2

(12) United States Patent
Hu et al.

(10) Patent No.: US 12,090,192 B2
(45) Date of Patent: Sep. 17, 2024

(54) APPLICATION OF RyR2 PROTEIN OR RECOMBINANT RyR2 PROTEIN IN PREPARING ANTI-HEART FAILURE MEDICAMENT

(71) Applicant: PHARCHOICE THERAPEUTICS INC, Shanghai (CN)

(72) Inventors: Shi Hu, Shanghai (CN); Wenyan Fu, Shanghai (CN)

(73) Assignee: PHARCHOICE THERAPEUTICS INC, Shanghai (CN)

( * ) Notice: Subject to any disclaimer, the term of this patent is extended or adjusted under 35 U.S.C. 154(b) by 876 days.

(21) Appl. No.: 17/054,073

(22) PCT Filed: Jul. 8, 2019

(86) PCT No.: PCT/CN2019/095015

§ 371 (c)(1), (2) Date: Nov. 9, 2020

(87) PCT Pub. No.: WO2020/011120

PCT Pub. Date: Jan. 16, 2020

(65) Prior Publication Data

US 2021/0138030 A1 May 13, 2021

(30) Foreign Application Priority Data

Jul. 9, 2018 (CN) ......................... 201810744453.3

(51) Int. Cl.

| | |
|---|---|
| ***C07K 14/705*** | (2006.01) |
| ***A61K 38/17*** | (2006.01) |
| ***A61P 9/04*** | (2006.01) |
| ***C12N 15/86*** | (2006.01) |

(52) U.S. Cl.

CPC .............. *A61K 38/177* (2013.01); *A61P 9/04* (2018.01); *C12N 15/86* (2013.01)

(58) Field of Classification Search

CPC .......... A61K 38/177; A61P 9/04; C12N 15/86

See application file for complete search history.

(56) References Cited

U.S. PATENT DOCUMENTS 9,220,755 B2 * 12/2015 Chakraborty ........ A61K 38/191
2010/0120628 A1 * 5/2010 Belouchi ................. G16B 5/00 506/9

OTHER PUBLICATIONS

Drumm et al, Genetic Variation and Clinical Heterogeneity in Cystic Fibrosis, Annu. Rev. Pathol. Mech. Dis., 2012, 7, pp. 267-282 (Year: 2012).*

Yampolsky et al, The Exchangeability of Amino Acids in Proteins, Genetics, 2005, 170, pp. 1459-1472. (Year: 2005).*

XP-002493145, Sven T. Pleger, et al., Stable Myocardial-Specific AAV6-S100A1 Gene Therapy Results in Chronic Functional Heart Failure Rescue, Circulation, 2007, pp. 2506-2515.

* cited by examiner

*Primary Examiner* — Julie Ha
*Assistant Examiner* — Kristina M Hellman
(74) *Attorney, Agent, or Firm* — Bayramoglu Law Offices LLC

(57) ABSTRACT

An application of a RyR2 protein or a recombinant RyR2 protein in preparing an anti-heart failure medicament is provided. The recombinant RyR2 protein is a naturally occurring RyR2 protein fragment or a mutant, such as a SPRY1 domain protein, a P1 domain protein, a SPRY2 domain protein, a SPRY3 domain protein, a Handle domain protein, an HD1 domain protein, an HD2 domain protein, a central domain protein, an EF-hand domain protein, a U-motif protein, a P2 domain protein, a P2 domain fragment protein-1, a P2 domain fragment protein-2 derived from a natural RyR2 protein or a P2 mutant derived from the natural RyR2 protein. The exogenous recombinant RyR2 protein is highly expressed in both normal small animal and diseased small animal models, so that the left ventricular ejection fraction of experimental animals is improved varying degrees compared with that of a control group.

6 Claims, 5 Drawing Sheets

Specification includes a Sequence Listing.

FIG. 1

APPLICATION OF RyR2 PROTEIN OR RECOMBINANT RyR2 PROTEIN IN PREPARING ANTI-HEART FAILURE MEDICAMENT

CROSS REFERENCE TO THE RELATED APPLICATIONS

This application is the national phase entry of International Application No. PCT/CN2019/095015, filed on Jul. 8, 2019, which is based upon and claims priority to Chinese Patent Application No. 201810744453.3, filed on Jul. 9, 2018, the entire contents of which are incorporated herein by reference.

TECHNICAL FIELD

The present invention relates to the technical field of biomedical engineering, and in particular to a recombinant ryanodine receptor type 2 (RyR2) protein used for enhancing contractility of cardiomyocytes, a polynucleotide sequence encoding the recombinant RyR2 protein, a vector and a medicament containing the recombinant RyR2 protein, and an application thereof.

BACKGROUND

Heart failure is the final stage of most cardiac diseases, which is one of the main causes contributing to human morbidity and mortality. The incidence rate of heart failure is increasing worldwide. Although the current medicine treatment has played a certain role in controlling the symptoms and mortality of heart failure, it cannot fundamentally reverse the development of the disease. 50% of heart failure patients will die within 5 years. At the cellular level, heart failure is mainly characterized by abnormal contraction and abnormal rhythm of cardiomyocytes.

Muscle tissue, which can be considered as the largest organ of vertebrates, can be divided into skeletal muscle tissue, myocardial tissue and smooth muscle tissue. Both skeletal muscle tissue and myocardial tissue belong to striated muscle tissue and have similar biological regulation effect. For example, skeletal muscle cells and cardiomyocytes have very similar process of excitation-contraction coupling. Membrane depolarization of myocytes and activated L-type voltage-gated calcium channel cause calcium to flow into the cytoplasm (sarcoplasm) of myocytes. The increased calcium concentration in cytoplasm can further activate ryanodine receptors (RyR) through the mechanism of calcium-induced calcium release (CICR). This leads to the release of calcium from sarcoplasmic reticulum (SR), and thus leads to a further rapid increase in calcium concentration of cytoplasm. Calcium ions diffuse through the cytoplasm and bind to actin (part of contractile proteins), such as troponin C, causing myocytes to contract. After contraction, the sarcoplasmic reticulum retrieves calcium ions and finally removes calcium in the cytoplasm mainly through the action of sarcoplasmic/endoplasmic reticulum calcium ATPase (SERCA). These biological processes are basically the same in skeletal muscle cells and cardiomyocytes, but there also exist some minor differences involved in these biological processes. For example, although RyR1 protein is a major release channel of calcium from the sarcoplasmic reticulum in skeletal muscle cells, RyR2 is dominant in cardiomyocytes. Similarly, SERCA in skeletal muscle cells is SERCA1a, while SERCA2a is specific in cardiomyocytes.

The calcium cycling and calcium homeostasis of cardiomyocytes are maintained by several key proteins. The disorder of calcium cycling leads to a variety of myocyte pathological processes, such as cardiac insufficiency, contractile ventricular dysfunction, arrhythmia, heart failure, cardiogenic shock, myocardial infarction and cardiac valve dysfunction. Ryanodine receptor type 2 (RyR2, UniProtKB No. Q92736) is a major calcium release channel in sarcoplasmic reticulum of cardiomyocytes. The amount of calcium ions released through RyR2 determines the amplitude of calcium transients, and the contractility of cardiomyocytes depends on the amplitude of calcium transients. In the pathological process of heart failure, previous studies showed that abnormal modification of RyR2 specific sites could be observed in heart failure patients and disease animal models, such as phosphorylation at residue serine 2808 and residue serine 2814 of RyR2 (Wehrens X H T, Lehnart S E, Reiken S, et al. Ryanodine receptor/calcium release channel PKA phosphorylation: a critical mediator of heart failure progression[J]. Proceedings of the National Academy of Sciences, 2006, 103(3): 511-518; Respress J L, van Oort R J, Li N, et al. Role of RyR2 phosphorylation at 52814 during heart failure progression[J]. Circulation Research, 2012: CIRCRESAHA. 112.268094.). It is generally believed that the abnormal modification of RyR2 specific sites leads to some changes in protein conformation, resulting in the dissociation of a channel-switch protein, FK506-binding protein 12.6 (FKBP12.6), increasing the probability of calcium channel opening, reducing the number of calcium ions released each time, and enhancing the pathological process of calcium leak.

Therefore, it is an urgent scientific challenge to reduce abnormal modification of RyR2 in myocardial pathological process by biomedical means.

SUMMARY

The objective of the present invention is to provide a novel recombinant ryanodine receptor type 2 (RyR2) protein capable of enhancing the contractility of cardiomyocytes, a polynucleotide sequence encoding the recombinant RyR2 protein, a vector and a medicament containing the recombinant RyR2 protein, and an application thereof.

A first aspect of the present invention provides a recombinant RyR2 protein, which is a naturally occurring RyR2 protein fragment or a mutant, and the length of the fragment or mutant is not less than 15 consecutive amino acid residues.

The recombinant RyR2 protein of the present invention is a positive inotropic peptide, which exhibits the ability to enhance the contractility of cardiomyocytes and/or to rebalance the calcium cycling.

In a preferred embodiment of the present invention, the fragment or the mutant may enhance cardiac function, and the fragment or the mutant has at least one function including, but not limited to, antiarrhythmia, antiapoptosis, reducing a spontaneous calcium spark frequency in cardiomyocytes, preventing and/or reducing calcium leak from sarcoplasmic reticulum, and restoring a hemodynamic function in individuals with heart failure.

Preferably, the recombinant RyR2 protein includes a SPRY1 domain protein, a P1 domain protein, a SPRY2 domain protein, a SPRY3 domain protein, a Handle domain protein, an HD1 domain protein, an HD2 domain protein, a central domain protein, an EF-hand domain protein, a U-motif protein, a P2 domain protein, a P2 domain fragment protein-1 and a P2 domain fragment protein-2. These fragments are derived from a natural RyR2 protein.

A second aspect of the present invention provides a gene encoding a recombinant RyR2 protein, preferably, a gene encoding a protein including a SPRY1 domain protein, a P1 domain protein, a SPRY2 domain protein, a SPRY3 domain protein, a Handle domain protein, an HD1 domain protein, an HD2 domain protein, a central domain protein, an EF-hand domain protein, a U-motif protein, a P2 domain protein, a P2 domain fragment protein-1 and a P2 domain fragment protein-2. These fragments are derived from the natural RyR2 protein.

In a preferred embodiment of the present invention, cardiac biological function can be enhanced by using the recombinant RyR2 protein or a polynucleotide encoding the recombinant RyR2 protein. The cardiac biological function is at least one selected from the group consisting of antiarrhythmia, antiapoptosis, reducing a spontaneous calcium spark frequency in cardiomyocytes, preventing and/or reducing calcium leak from sarcoplasmic reticulum, and restoring a hemodynamic function in individuals with heart failure.

Therefore, the recombinant RyR2 protein or the polynucleotide encoding the recombinant RyR2 protein can be used to achieve anti-arrhythmic function on the cardiomyocytes, and therefore, preferably, to protect cardiomyocytes and cardiac tissues from arrhythmias, especially catecholamine-evoked arrhythmias, such as ventricular arrhythmia associated with sudden cardiac death.

Additionally, the recombinant RyR2 protein or the polynucleotide encoding the recombinant RyR2 protein can also protect subjects from lethal ventricular tachyarrhythmias, such as adrenergic receptor-mediated lethal ventricular tachycardias and catecholamine-mediated lethal ventricular tachyarrhythmias.

In a further preferred embodiment, the recombinant RyR2 protein or the polynucleotide encoding the recombinant RyR2 protein also has an ability to reduce a calcium spark frequency in cardiomyocytes.

In a preferred embodiment of the present invention, when the recombinant RyR2 protein is the SPRY1 domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 1; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 2.

In a preferred embodiment of the present invention, when the recombinant RyR2 protein is the P1 domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 3; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 4.

In a preferred embodiment of the present invention, when the recombinant RyR2 protein is the SPRY2 domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 5; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 6.

In a preferred embodiment of the present invention, when the recombinant RyR2 protein is the SPRY3 domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 7; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 8.

In a preferred embodiment of the present invention, when the recombinant RyR2 protein is the Handle domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 9; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 10.

In a preferred embodiment of the present invention, when the recombinant RyR2 protein is the HD1 domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 11; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 12.

In a preferred embodiment of the present invention, when the recombinant RyR2 protein is the HD2 domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 13; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 14.

In a preferred embodiment of the present invention, when the recombinant RyR2 protein is the central domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 15; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 16.

In a preferred embodiment of the present invention, when the recombinant RyR2 protein is the EF-hand domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 17; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 18.

In a preferred embodiment of the present invention, when the recombinant RyR2 protein is the U-motif protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 19; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 20.

In a preferred embodiment of the present invention, when the recombinant RyR2 protein is the P2 domain protein derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 21; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 22.

In a preferred embodiment of the present invention, when the recombinant RyR2 protein is the P2 domain fragment protein-1 derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 23; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 24.

In a preferred embodiment of the present invention, when the recombinant RyR2 protein is the P2 domain fragment protein-2 derived from the natural RyR2 protein, an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 25; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 26.

It should be noted that in a preferred embodiment of the present invention, a fragment protein derived from a P2 domain of the natural RyR2 protein includes at least a P2 core peptide segment, and an amino acid sequence of the core peptide segment has at least 60%, preferably at least 65%, preferred at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 27; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 28. Preferably, the core peptide segment includes a RyR2 S2808 site and/or a RyR2 S2814 site.

In a preferred embodiment of the present invention, the recombinant RyR2 protein is a P2 mutant derived from the natural RyR2 protein, and an amino acid sequence of the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to an amino acid sequence shown in SEQ ID NO. 29; a polynucleotide sequence encoding the protein has at least 60%, preferably at least 65%, preferably at least 70%, more preferably at least 75%, more preferably at least 80%, more preferably at least 85%, even more preferably at least 90%, even more preferably at least 95% and most preferably at least 99% identity to a polynucleotide sequence shown in SEQ ID NO. 30.

A third aspect of the present invention provides a delivery vector of a RyR2 gene coding the recombinant RyR2 protein, and the delivery vector can be recombined with the RyR2 gene and integrated into a genome of cardiomyocytes. In order to adapt to an expression of the RyR2 gene in cardiac tissues, a cardiac tissue-specific promoter is arranged on the delivery vector.

The vector is one selected from the group consisting of a plasmid vector, a cosmid vector, a phage vector (such as a λ phage, a filamentous phage vector), a viral vector, a virus-like particle and a bacterial spore. Preferably, the vector is the viral vector, and the viral vector is one selected from the group consisting of adenovirus vector, adeno-associated virus (AAV) vector, α-virus vector, herpes virus vector, measles virus vector, poxvirus vector, vesicular stomatitis virus vector, retroviral vector and lentiviral vector. Most preferably, the vector is the AAV vector, such as AAV6 and AAV9.

A suitable dosage of the viral vector is $5\times10^{9}$-$1\times10^{15}$ tvp, a more preferred dosage is $1\times10^{11}$-$1\times10^{13}$ tvp, and a most preferred dosage is $1\times10^{12}$ tvp.

The expression of a RyR2 protein is controlled by the cardiac tissue-specific promoter, i.e., a preferred vector also includes the cardiac tissue-specific promoter. Preferably, the cardiac tissue-specific promoter is selected from but not limited to a cardiac actin enhancer/elongation factor 1 promoter and a cytomegolo-virus enhancer/myosin light chain ventricle 2 promoter.

A fourth aspect of the present invention provides an anti-heart failure medicament composition, the medicament composition includes two forms: one containing a recombinant RyR2 protein, and further including a medically acceptable excipient, a carrier or a diluent, and the other containing a RyR2 gene, and further including a delivery vector and a medicinal carrier.

In a preferred embodiment of the present invention, an intracellular level of the recombinant RyR2 protein is elevated in at least 30% of cells in individual cardiac tissues, and a number of cardiac cells specifically expressing a RyR2 protein will depend on an underlying disease condition. Preferably, in a treated cardiac region, the intracellular level of the RyR2 protein is elevated as described above.

The intracellular level of the recombinant RyR2 protein is elevated in the cells of the individual cardiac tissues, further mediating a reduction in a level of a chemical modification at a specific site of the endogenous RyR2 protein in the cells. Preferably, the modification is one selected from the group consisting of phosphorylation, nitrification, methylation and acetylation. Most preferably, the site is S2808 and/or S2814, and the modification is the phosphorylation.

In an embodiment of the present invention, the anti-heart failure medicament composition is administered orally, intravenously, intramucosally, intraarterially, intramuscularly, or intracoronally. Preferably, the anti-heart failure medicament composition is administered intravenously.

In a further embodiment of the present invention, the intracellular level of the recombinant RyR2 protein is elevated for at least 7 days, more preferably for at least 14 days, and even more preferably for at least 28 days. This result is preferably obtained as a result of a single administration or a repeated administration.

In the present invention, a subject individual is healthy, or has a heart disease, or has a risk for the heart disease. The mechanism of the heart disease is related to the steady-state destruction of calcium cycling in cardiomyocytes and/or the cardiomyocyte contractile dysfunction. In a preferred embodiment, the heart disease is selected from post-ischemic contractile dysfunction, preferably post-ischemic contractile right and/or left ventricular dysfunction and congestive heart failure, preferably compensated and/or decompensated congestive heart failure, cardiogenic shock, septic shock, myocardial infarction, cardiomyopathy, cardiac valve dysfunction and ventricular disease, etc. For example, the heart disease is acute/chronic right ventricular dysfunction. More preferably, the heart disease is primary/secondary cardiomyopathy. The primary cardiomyopathy is preferably derived from hereditary cardiomyopathy and cardiomyopathy caused by spontaneous mutations. The secondary cardiomyopathy is preferably derived from ischemic cardiomyopathy caused by free arteriosclerosis, dilated cardiomyopathy caused by infection or poisoning, hypertensive heart disease caused by pulmonary artery and/or arterial hypertension, and cardiac valve disease.

A fifth aspect of the present invention provides an application of a RyR2 protein, a recombinant RyR2 protein or a gene encoding the RyR2 protein and the recombinant RyR2 protein in preparing an anti-heart failure medicament.

Preferably, the anti-heart failure medicament is a medicament increasing an intracellular level of the RyR2 protein in cardiac tissues, or reducing a level of a chemical modification at a specific site of the RyR2 protein in cells.

Preferably, the specific site of the RyR2 protein is at least one selected from the group consisting of S2808 and S2814, and the chemical modification is one selected from the group consisting of phosphorylation, nitrification, methylation and acetylation.

Therefore, a sixth aspect of the present invention provides an application of a RyR2 protein, a recombinant RyR2 protein or a polynucleotide of a gene encoding the RyR2 protein and the recombinant RyR2 protein in treating a heart disease by enhancing cardiac function of a subject. The subject has a heart disease, or has a risk for the heart disease. In a treatment window, it is used to increase a concentration of the RyR2 protein in individual cardiomyocytes.

Preferably, the recombinant RyR2 protein or the polynucleotide encoding the recombinant RyR2 protein is used for treating the heart disease by enhancing cardiac contractility of an individual with or at a risk of developing the heart disease, and for increasing the concentration of the RyR2 protein in the individual cardiomyocytes within the treatment window.

The cardiac function may enhance muscle contractile function by improving cardiac muscle function, contractile performance and/or calcium processing capacity. In a preferred embodiment, the cardiac function is enhanced by at least 15%, preferably at least 25%, more preferably at least 35%, most preferably at least 45%, and most preferably at least 50% compared to a control group.

Preferably, the control group is set as muscle function, contractile performance and/or calcium processing capacity of healthy volunteers, or an average value of a group of healthy volunteers. In a preferred embodiment, the cardiac function is enhanced by the recombinant RyR2 protein or the polynucleotide encoding the recombinant RyR2 protein, and the function exhibited by the RyR2 protein is at least one selected from the group consisting of an antiarrhythmia potential, an antiapoptosis potential, an ability to reduce a calcium spark frequency, an ability to prevent and/or reduce calcium leak from sarcoplasmic reticulum, and preferably an ability to restore a hemodynamic function in individuals with heart failure.

A seventh aspect of the present invention provides a method for increasing a concentration of a RyR2 protein in cardiomyocytes. The concentration of the RyR2 protein in the cardiomyocytes is increased by using a recombinant vector, and the recombinant vector includes a polynucleotide encoding a recombinant RyR2 protein or the recombinant RyR2 protein.

The Advantages of the Present Invention

The present invention provides an application of a RyR2 protein or a recombinant RyR2 protein in preparing an anti-heart failure medicament. The recombinant RyR2 protein is derived from a natural RyR2 protein fragment or mutant. Experiments prove that the exogenous recombinant RyR2 protein has high expression levels in both normal small animal model and diseased small animal model, so that the left ventricular ejection fraction of the experimental animals is improved to different degrees compared with that of a control group. Meanwhile, the animals of disease model can reduce the ventricular tachyarrhythmias triggered by (3-adrenaline to different degrees, and the cardiac function of each treatment group has different degrees of recovery. Therefore, the recombinant RyR2 protein of the present invention can effectively relieve and treat heart failure, and can be applied in preparing a medicament for treating heart failure, and has broad clinical application prospects.

BRIEF DESCRIPTION OF THE DRAWINGS

FIG. 1 is a schematic diagram showing a construction of a viral vector;

DETAILED DESCRIPTION OF THE EMBODIMENTS

Figure 2:
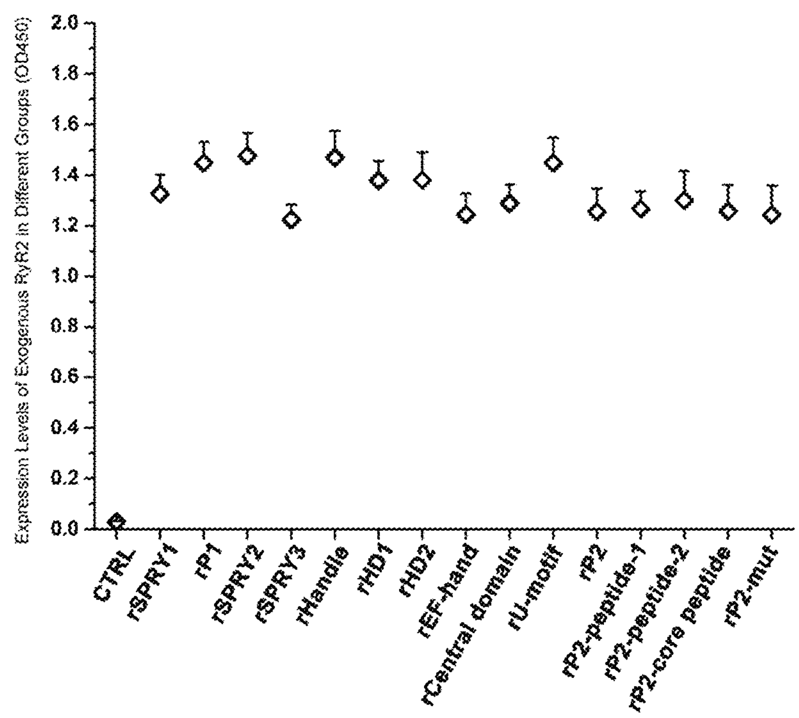
FIG. 2 is a diagram showing expression levels of exogenous recombinant RyR2 proteins in different treatment groups of normal mice.

The following embodiments and experimental examples further illustrate the present invention, which should not be interpreted as a limitation of the present invention. The embodiments do not include detailed descriptions of conventional methods, such as methods used to construct vectors and plasmids, methods of inserting genes encoding proteins into such vectors and plasmids, or methods of introducing plasmids into host cells. Such methods are well known to those of ordinary skill in the art and have been described in numerous publications, including: Sambrook, J., Fritsch, E. F. and Maniais, T. (1989) Molecular Cloning: A Laboratory Manual, $2^{nd}$ edition, Cold spring Harbor Laboratory Press.

Figure 1:
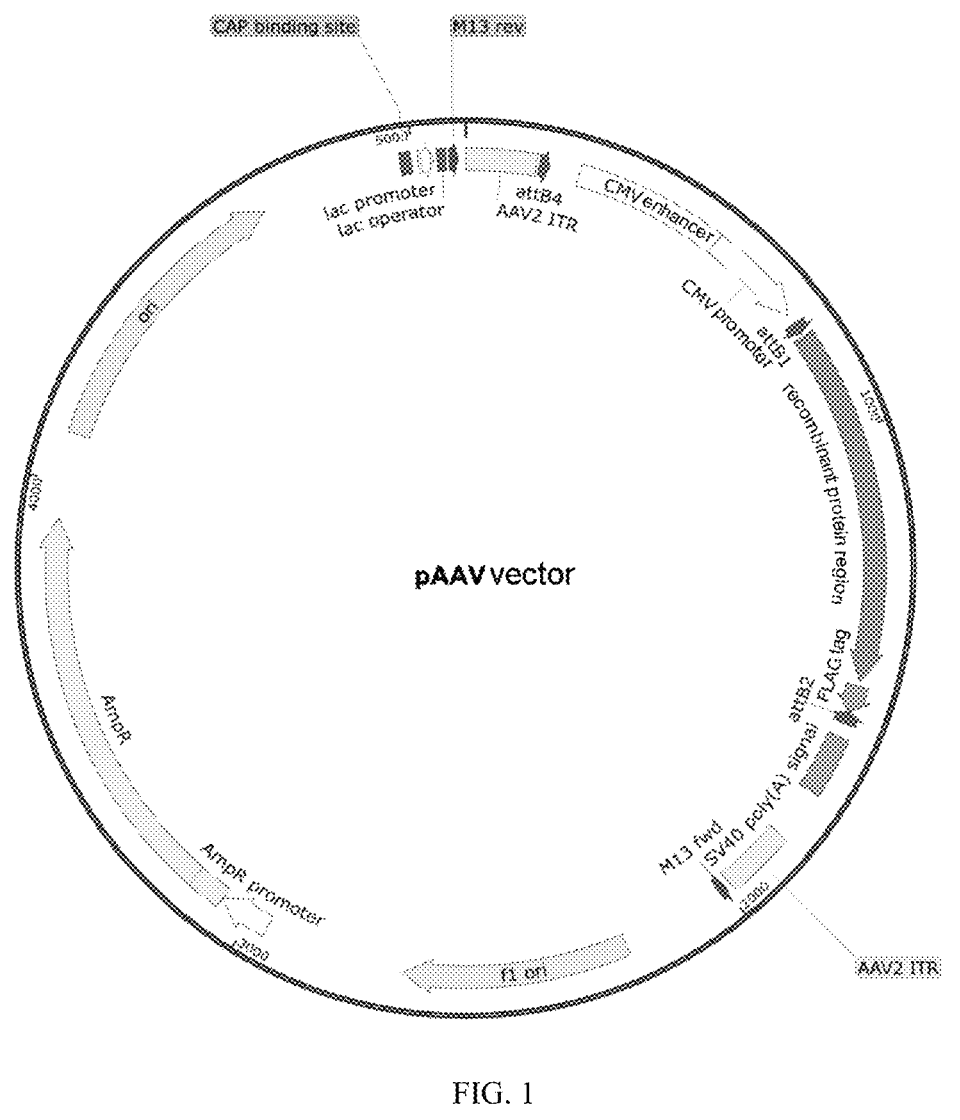

Embodiment 1. Effects of Myocardial-Specific Exogenous Expressions of RyR2 Proteins on Cardiac Functions of Normal Small Animal Model In order to detect the enhancing effect of AAV9-mediated RyR2 cDNA myocardial gene delivery on cardiac function, normal C57B/6 mice aged 6 months are divided into a treatment group and a control group. The intracellular deliveries of all recombinant RyR2 proteins are carried out using pAAV vectors with FLAG tags added to the C-terminals to facilitate detection. The construction of a viral vector is shown in FIG. 1. The polynucleotide encoding the recombinant protein described below is the recombinant protein region of the vector as shown in FIG. 1, with an ATG initiation codon added at the 5' end if necessary. The specific grouping is described as follows.

The control group (CTRL) is a virus-empty group; the rSPRY1 group is a group expressing a recombinant SPRY domain protein, i.e., a polynucleotide of the recombinant protein region of the vector shown in FIG. 1 is shown as SEQ ID NO. 2. The group rP1 is a group expressing a recombinant P1 domain protein, i.e., a polynucleotide of the recombinant protein region of the vector shown in FIG. 1 is shown as SEQ ID No. 4. The rSPRY2 group is a group expressing a recombinant SPRY2 domain protein, i.e., a polynucleotide of the recombinant protein region of the vector shown in FIG. 1 is shown as SEQ ID No. 6. The rSPRY3 group is a group expressing a recombinant SPRY3 domain protein, i.e., a polynucleotide of the recombinant protein region of the vector shown in FIG. 1 is shown as SEQ ID No. 8 The rHandle group is a group expressing a recombinant Handle domain protein, i.e., a polynucleotide of the recombinant protein region of the vector shown in FIG. 1 is shown as SEQ ID No. 10. The rHD1 group is a group expressing a recombinant HD1 domain protein, i.e., a polynucleotide of the recombinant protein region of the vector shown in FIG. 1 is shown as SEQ ID No. 12. The rHD2 group is a group expressing a recombinant HD2 domain protein, i.e., a polynucleotide of the recombinant protein region of the vector shown in FIG. 1 is shown as SEQ ID No. 14. The rCentral domain group is a group expressing a recombinant central domain protein, i.e., a polynucleotide of the recombinant protein region of the vector shown in FIG. 1 is shown as SEQ ID No. 16. The rEF-hand group is a group expressing an EF-hand domain protein, i.e., a polynucleotide of the recombinant protein region of the vector shown in FIG. 1 is shown as SEQ ID No. 18. The rU-motif group is a group expressing a U-domain protein, i.e., a polynucleotide of the recombinant protein region of the vector shown in FIG. 1 is shown as SEQ ID No.

20. The rP2 group is a group expressing a P2 domain protein, i.e., a polynucleotide of the recombinant protein region of the vector shown in FIG. 1 is shown as SEQ ID No. 22. The rP2-peptide-1 group is a group expressing a P2 domain fragment-1, i.e., a polynucleotide of the recombinant protein region of the vector shown in FIG. 1 is shown as SEQ ID No. 24. The rP2-peptide-2 group is a group expressing a P2 domain fragment-2, i.e., a polynucleotide of the recombinant protein region of the vector shown in FIG. 1 is shown as SEQ ID No. 26. The rP2-Core-peptide group is a group expressing a P2 domain core fragment, i.e., a polynucleotide of the recombinant protein region of the vector shown in FIG. 1 is shown as SEQ ID No. 28. The rP2-mut group is a group expressing a P2 domain mutant, i.e., a polynucleotide of the recombinant protein region of the vector shown in FIG. 1 is shown as SEQ ID No. 30.

Specific detection techniques for viral cardiomyocyte infection and protein expression refer to the non-patent document Voelkers et al. Circ Res (2011) 108: 27-39. Method for evaluating cardiac function by echocardiography refers to the non-patent document Most et al. JCI (2004) 114: 1550-1563. Methods for constructing viral vectors and utilizing myocardial-specific promoters refer to the non-patent document Pleger et al. Science Translational Medicine (2011) 3, 92ra64. The injection dose of virus particles is $1\times10^{12}$ tvp (total virus particles; tvp). The expression levels of myocardial-exogenous RyR2 proteins are detected by ELSIA or Western Blot.

The expression levels of the myocardial-exogenous RyR2 proteins of mice in different groups are shown in FIG. 2. FIG. 2 shows that, compared with the control group, each exogenous recombinant RyR2 gene has a relative high expression level in myocardial tissue of mice.

Figure 3:
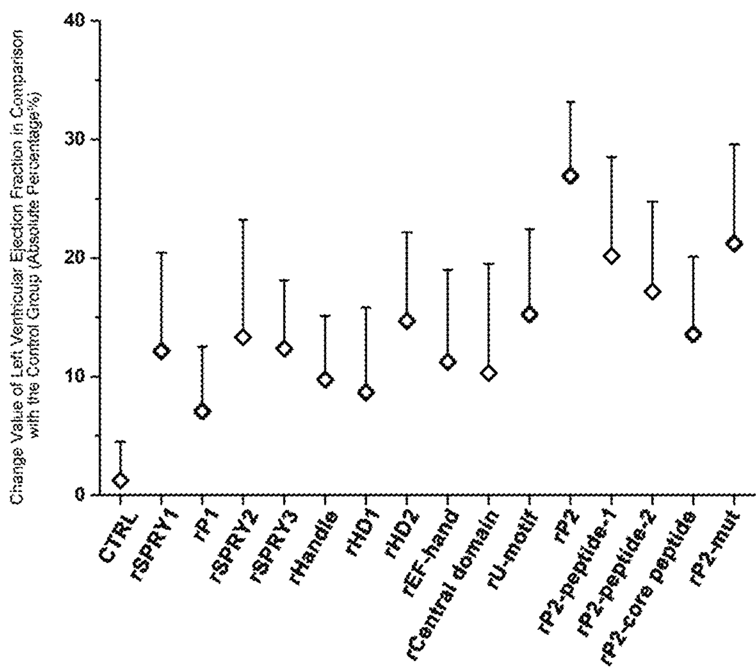
FIG. 3 is a diagram showing results of left ventricular ejection fraction in different treatment groups of normal mice.

The left ventricular ejection fractions (LVEF) of mice in different groups are shown in FIG. 3. The results show that the left ventricular ejection fraction of mice in each treatment group is also increased to various degrees compared with the control group, indicating that each exogenous recombinant RyR2 protein can improve the cardiac pumping capacity and help prevent heart failure.

Embodiment 2. Effects of Myocardial-Specific Exogenous Expressions of RyR2 Proteins on Cardiac Functions of Diseased Small Animal Model Further, the enhancing effect of AAV9-mediated RyR2 cDNA myocardial gene delivery on cardiac function is evaluated in the disease model. The steps are described as follows.

Firstly, the 6-month-old C57B/6 mice model with myocardial infarction is established. The model is established using temporary occlusion of the left anterior coronary artery with reference to the non-patent document Brinks et al. Circ Res (2010) 107: 1140-1149. Then, the mice are divided into a treatment group and a control group, and the C-terminals of all the RyR2 proteins are added with FLAG tags to facilitate detection. The specific construction method is the same as that of embodiment 1. The techniques for viral cardiomyocyte infection and methods for constructing viral vectors and utilizing myocardial-specific promoters are the same as those of embodiment 1. The injection dosage of virus particles is $1\times10^{12}$ tvp (total virus particles; tpv). The expression levels of myocardial-exogenous RyR2 proteins are detected by ELSIA or Western Blot.

Figure 4:
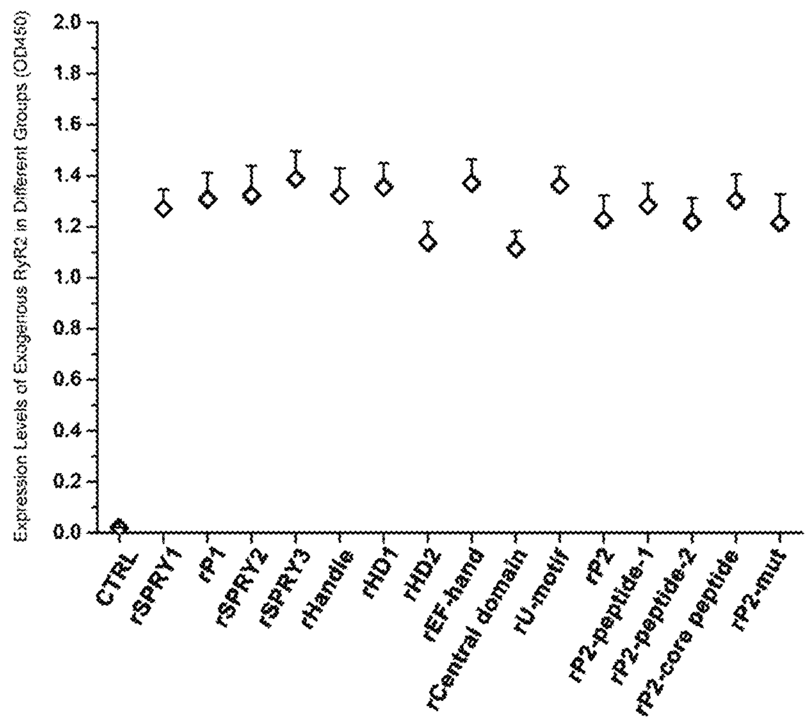
FIG. 4 is a diagram showing expression levels of the exogenous recombinant RyR2 proteins in different treatment groups of disease model mice.

The expression levels of the myocardial-exogenous RyR2 proteins of disease model mice in different groups are shown in FIG. 4. FIG. 4 shows that, compared with the control group, each exogenous recombinant RyR2 gene has a relative high expression level in myocardial tissue of mice.

Figure 5:
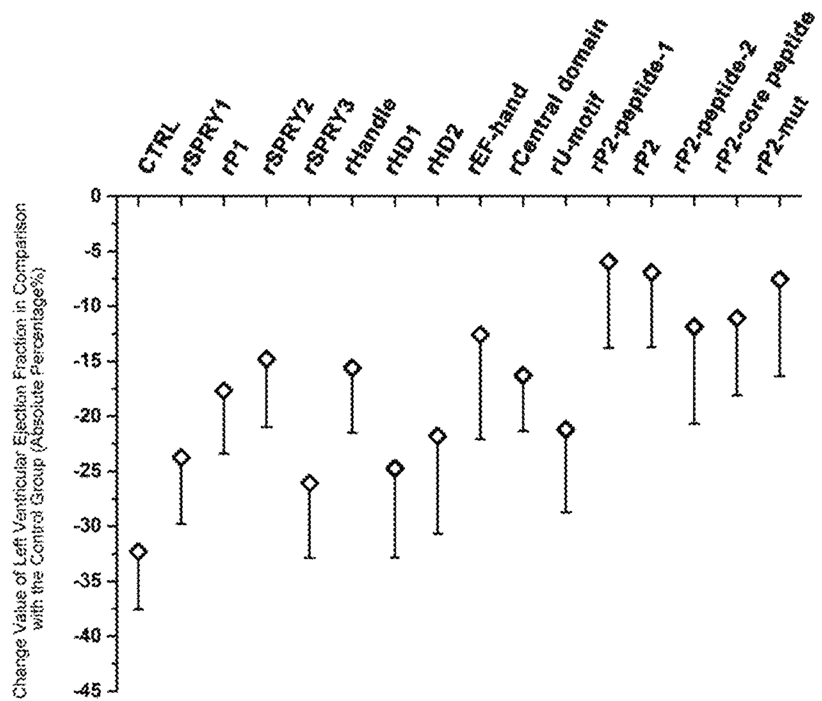
FIG. 5 is a diagram showing results of left ventricular ejection fractions in different treatment groups of disease model mice.

The left ventricular ejection fractions (LVEF) of disease model mice in different groups are shown in FIG. 5. The results show that the left ventricular ejection fraction of mice in each treatment group is increased to various degrees compared with the control group. The increase degree of the P2 domain fragment-1 recombinant protein is the largest, followed by the P2 domain recombinant protein, indicating that each exogenous recombinant RyR2 protein can improve the cardiac pumping capacity, has significant effect on the treatment of heart failure, and contributes to the recovery of cardiac function.

Figure 6:
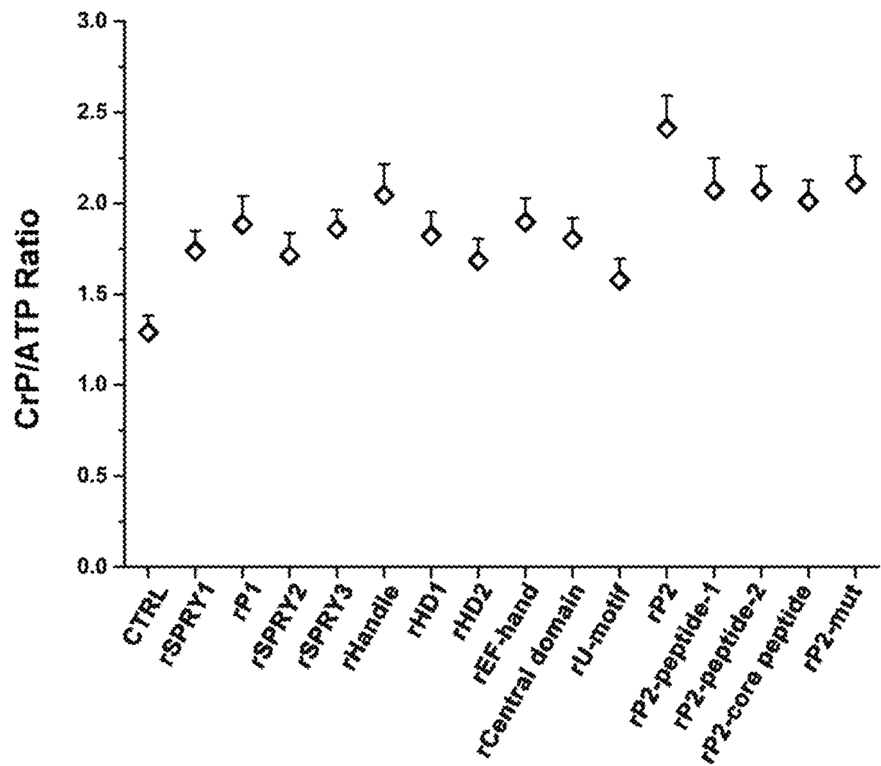
FIG. 6 is a diagram showing results of Crp/ATP ratio in different treatment groups of disease model mice.

FIG. 6 shows the CRP/ATP ratio level of mice in each disease model treatment group. The results show that the cardiac function of mice in each disease model treatment group has different degrees of recovery, and the recovery degree of the treatment group of P2 domain recombinant protein is the largest, increased by 67%, corresponding to the results in FIG. 5.

Figure 7A:
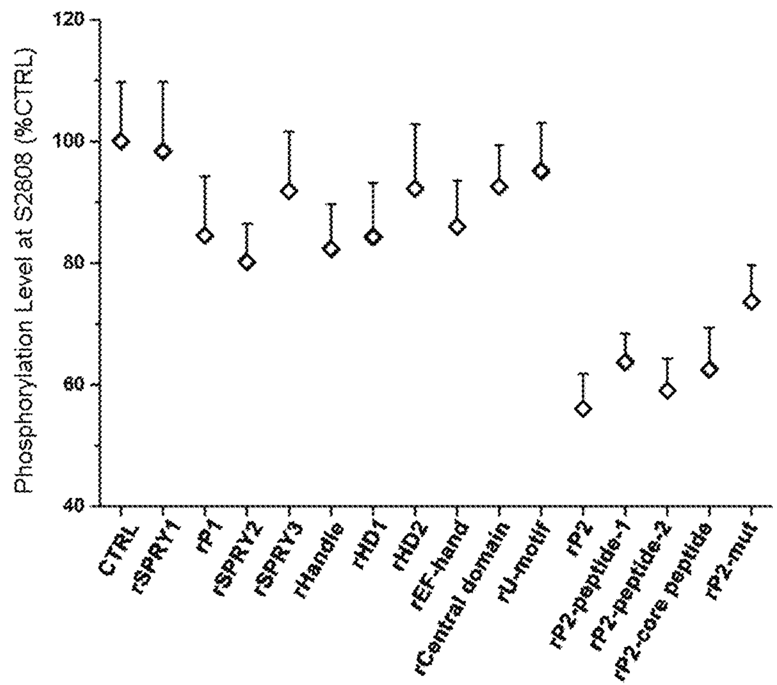
FIG. 7A is a diagram showing results of phosphorylation degrees at RyR2 2808 in different treatment groups of disease model mice.
Figure 7B:
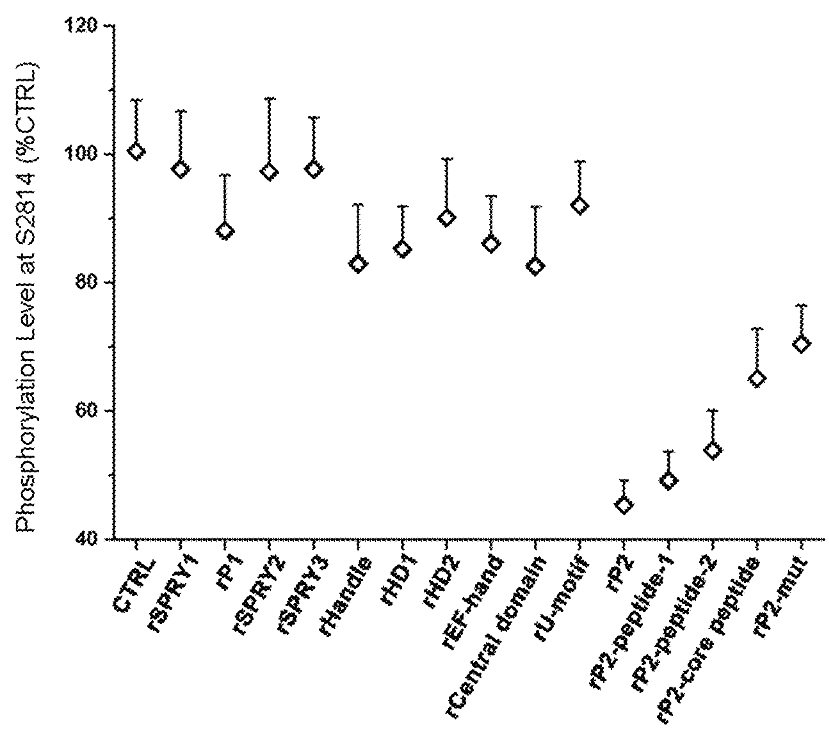
FIG. 7B is a diagram showing results of phosphorylation degrees at RyR2 2814 in different treatment groups of disease model mice.

FIGS. 7A-B show that S2808 and S2814 of mice in each disease model treatment group are detected by ELISA (Amino acid coding referring to literature: Shan J. et al, J Clin Invest. 2010 December; 120 (12): 4375-87).

The preferred embodiments of the present invention have been specifically described above, but the present invention is not limited to the embodiments. A person skilled in the art can also make various equivalent modifications or substitutions without violating the spirit of the present invention. These equivalent modifications or substitutions shall all fall within the scope of claims of the present application.

What is claimed is:

1. A method for preparing an anti-heart failure medicament comprising the step of adding a recombinant ryanodine receptor type 2 (RyR2) protein mutant to a medicinal excipient, wherein the recombinant RyR2 protein mutant is a P2 domain fragment from a human RyR2 protein comprising the amino acid sequence of SEQ ID NO: 29.

2. A method for preparing an anti-heart failure medicament comprising the step of adding a gene sequence encoding a recombinant RyR2 protein mutant to a medicinal excipient, wherein the recombinant RyR2 protein mutant is a P2 domain fragment from a human RyR2 protein comprising the sequence in of SEQ ID NO: 30.

3. A delivery vector comprising a gene encoding a recombinant RyR2 protein mutant, wherein the recombinant RyR2 protein mutant is a P2 domain fragment from a human RyR2 protein comprising the sequence of SEQ ID NO:30 and a cardiac tissue-specific promoter.

4. The delivery vector according to claim 3, wherein the delivery vector is selected from the group consisting of a plasmid vector, a cosmid vector, a phage vector and a viral vector; and the viral vector is selected from the group consisting of adenovirus vector, adeno-associated virus (AAV) vector, a-virus vector, herpes virus vector, measles virus vector, poxvirus vector, vesicular stomatitis virus vector, retroviral vector and lentiviral vector.

5. An anti-heart failure medicament composition comprising a recombinant RyR2 protein mutant and a medically acceptable excipient, carrier or diluent, wherein the recombinant RyR2 protein mutant is a P2 domain fragment from a human RyR2 protein comprising the amino acid sequence of SEQ ID NO: 29.

6. The delivery vector according to claim 3, wherein the cardiac tissue-specific promoter is selected from the group consisting of a cardiac actin enhancer/elongation factor 1 promoter and a cytomegalovirus enhancer/myosin light chain ventricle 2 promoter.

* * * * *

SEQUENCE LISTING

```
<160> NUMBER OF SEQ ID NOS: 30

<210> SEQ ID NO 1
<211> LENGTH: 189
<212> TYPE: PRT
<213> ORGANISM: Artificial Sequence
<220> FEATURE:
<223> OTHER INFORMATION: The sequence is synthetized.

<400> SEQUENCE: 1

Val Ser Ser Met Arg Pro Asn Ile Phe Leu Gly Val Ser Glu Gly Ser
1               5                   10                  15

Ala Gln Tyr Lys Lys Trp Tyr Tyr Glu Leu Met Val Asp His Thr Glu
```

```
            20                  25                  30

Pro Phe Val Thr Ala Glu Ala Thr His Leu Arg Val Gly Trp Ala Ser
        35                  40                  45

Thr Glu Gly Tyr Ser Pro Tyr Pro Gly Gly Gly Glu Glu Trp Gly Gly
    50                  55                  60

Asn Gly Val Gly Asp Asp Leu Phe Ser Tyr Gly Phe Asp Gly Leu His
65                  70                  75                  80

Leu Trp Ser Gly Cys Ile Ala Arg Thr Val Ser Ser Pro Asn Gln His
                85                  90                  95

Leu Leu Arg Thr Asp Asp Val Ile Ser Cys Cys Leu Asp Leu Ser Ala
            100                 105                 110

Pro Ser Ile Ser Phe Arg Ile Asn Gly Gln Pro Val Gln Gly Met Phe
        115                 120                 125

Glu Asn Phe Asn Ile Asp Gly Leu Phe Phe Pro Val Val Ser Phe Ser
    130                 135                 140

Ala Gly Ile Lys Val Arg Phe Leu Leu Gly Gly Arg His Gly Glu Phe
145                 150                 155                 160

Lys Phe Leu Pro Pro Pro Gly Tyr Ala Pro Cys Tyr Glu Ala Val Leu
                165                 170                 175

Pro Lys Glu Lys Leu Lys Val Glu His Ser Arg Glu Tyr
            180                 185
```

<210> SEQ ID NO 2
<211> LENGTH: 567
<212> TYPE: DNA
<213> ORGANISM: Artificial Sequence
<220> FEATURE:
<223> OTHER INFORMATION: The sequence is synthetized.

<400> SEQUENCE: 2

```
gtgagcagca tgagacccaa catcttcctg ggcgtgagcg agggcagcgc ccagtacaag     60

aagtggtact acgagctgat ggtggaccac accgagccct tcgtgaccgc cgaggccacc    120

cacctgagag tgggctgggc cagcaccgag ggctacagcc cctaccccgg cggcggcgag    180

gagtggggcg gcaacggcgt gggcgacgac ctgttcagct acggcttcga cggcctgcac    240

ctgtggagcg gctgcatcgc cagaaccgtg agcagcccca accagcacct gctgagaacc    300

gacgacgtga tcagctgctg cctggacctg agcgccccca gcatcagctt cagaatcaac    360

ggccagcccg tgcagggcat gttcgagaac ttcaacatcg acggcctgtt cttccccgtg    420

gtgagcttca gcgccggcat caaggtgaga ttcctgctgg gcggcagaca cggcgagttc    480

aagttcctgc ccccccccgg ctacgccccc tgctacgagg ccgtgctgcc caaggagaag    540

ctgaaggtgg agcacagcag agagtac                                        567
```

<210> SEQ ID NO 3
<211> LENGTH: 205
<212> TYPE: PRT
<213> ORGANISM: Artificial Sequence
<220> FEATURE:
<223> OTHER INFORMATION: The sequence is synthetized.

<400> SEQUENCE: 3

```
Phe Thr Pro Ile Pro Val Asp Thr Ser Gln Ile Val Leu Pro Pro His
1               5                   10                  15

Leu Glu Arg Ile Arg Glu Lys Leu Ala Glu Asn Ile His Glu Leu Trp
            20                  25                  30

Val Met Asn Lys Ile Glu Leu Gly Trp Gln Tyr Gly Pro Val Arg Asp
```

```
        35                  40                  45

Asp Asn Lys Arg Gln His Pro Cys Leu Val Glu Phe Ser Lys Leu Pro
    50                  55                  60

Glu Gln Glu Arg Asn Tyr Asn Leu Gln Met Ser Leu Glu Thr Leu Lys
65                  70                  75                  80

Thr Leu Leu Ala Leu Gly Cys His Val Gly Ile Ser Asp Glu His Ala
                85                  90                  95

Glu Asp Lys Val Lys Lys Met Lys Leu Pro Lys Asn Tyr Gln Leu Thr
            100                 105                 110

Ser Gly Tyr Lys Pro Ala Pro Met Asp Leu Ser Phe Ile Lys Leu Thr
        115                 120                 125

Pro Ser Gln Glu Ala Met Val Asp Lys Leu Ala Glu Asn Ala His Asn
    130                 135                 140

Val Trp Ala Arg Asp Arg Ile Arg Gln Gly Trp Thr Tyr Gly Ile Gln
145                 150                 155                 160

Gln Asp Val Lys Asn Arg Arg Asn Pro Arg Leu Val Pro Tyr Thr Leu
                165                 170                 175

Leu Asp Asp Arg Thr Lys Lys Ser Asn Lys Asp Ser Leu Arg Glu Ala
            180                 185                 190

Val Arg Thr Leu Leu Gly Tyr Gly Tyr Asn Leu Glu Ala
        195                 200                 205


<210> SEQ ID NO 4
<211> LENGTH: 615
<212> TYPE: DNA
<213> ORGANISM: Artificial Sequence
<220> FEATURE:
<223> OTHER INFORMATION: The sequence is synthetized.

<400> SEQUENCE: 4

ttcaccccca tccccgtgga caccagccag atcgtgctgc ccccccacct ggagagaatc      60

agagagaagc tggccgagaa catccacgag ctgtgggtga tgaacaagat cgagctgggc     120

tggcagtacg gccccgtgag agacgacaac aagagacagc acccctgcct ggtggagttc     180

agcaagctgc ccgagcagga gagaaactac aacctgcaga tgagcctgga gaccctgaag     240

accctgctgg ccctgggctg ccacgtgggc atcagcgacg agcacgccga ggacaaggtg     300

aagaagatga agctgcccaa gaactaccag ctgaccagcg gctacaagcc cgcccccatg     360

gacctgagct tcatcaagct gacccccagc caggaggcca tggtggacaa gctggccgag     420

aacgcccaca acgtgtgggc cagagacaga atcagacagg gctggaccta cggcatccag     480

caggacgtga agaacagaag aaaccccaga ctggtgccct acaccctgct ggacgacaga     540

accaagaaga gcaacaagga cagcctgaga gaggccgtga gaaccctgct gggctacggc     600

tacaacctgg aggcc                                                      615


<210> SEQ ID NO 5
<211> LENGTH: 134
<212> TYPE: PRT
<213> ORGANISM: Artificial Sequence
<220> FEATURE:
<223> OTHER INFORMATION: The sequence is synthetized.

<400> SEQUENCE: 5

Arg Phe Arg Ile Phe Arg Ala Glu Lys Thr Tyr Ala Val Lys Ala Gly
1               5                   10                  15

Arg Trp Tyr Phe Glu Phe Glu Thr Val Thr Ala Gly Asp Met Arg Val
            20                  25                  30
```

```
Gly Trp Ser Arg Pro Gly Cys Gln Pro Asp Gln Glu Leu Gly Ser Asp
        35                  40                  45

Glu Arg Ala Phe Ala Phe Asp Gly Phe Lys Ala Gln Arg Trp His Gln
    50                  55                  60

Gly Asn Glu His Tyr Gly Arg Ser Trp Gln Ala Gly Asp Val Val Gly
65                  70                  75                  80

Cys Met Val Asp Met Asn Glu His Thr Met Met Phe Thr Leu Asn Gly
                85                  90                  95

Glu Ile Leu Leu Asp Asp Ser Gly Ser Glu Leu Ala Phe Lys Asp Phe
            100                 105                 110

Asp Val Gly Asp Gly Phe Ile Pro Val Cys Ser Leu Gly Val Ala Gln
        115                 120                 125

Val Gly Arg Met Asn Phe
    130


<210> SEQ ID NO 6
<211> LENGTH: 402
<212> TYPE: DNA
<213> ORGANISM: Artificial Sequence
<220> FEATURE:
<223> OTHER INFORMATION: The sequence is synthetized.

<400> SEQUENCE: 6

agattcagaa tcttcagagc cgagaagacc tacgccgtga aggccggcag atggtacttc      60

gagttcgaga ccgtgaccgc cggcgacatg agagtgggct ggagcagacc cggctgccag     120

cccgaccagg agctgggcag cgacgagaga gccttcgcct tcgacggctt caaggcccag     180

agatggcacc agggcaacga gcactacggc agaagctggc aggccggcga cgtggtgggc     240

tgcatggtgg acatgaacga gcacaccatg atgttcaccc tgaacggcga gatcctgctg     300

gacgacagcg gcagcgagct ggccttcaag gacttcgacg tgggcgacgg cttcatcccc     360

gtgtgcagcc tgggcgtggc ccaggtgggc agaatgaact tc                        402


<210> SEQ ID NO 7
<211> LENGTH: 398
<212> TYPE: PRT
<213> ORGANISM: Artificial Sequence
<220> FEATURE:
<223> OTHER INFORMATION: The sequence is synthetized.

<400> SEQUENCE: 7

Asn Arg Asp Ile Thr Met Trp Leu Ser Lys Arg Leu Pro Gln Phe Leu
1               5                   10                  15

Gln Val Pro Ser Asn His Glu His Ile Glu Val Thr Arg Ile Asp Gly
            20                  25                  30

Thr Ile Asp Ser Ser Pro Cys Leu Lys Val Thr Gln Lys Ser Phe Gly
        35                  40                  45

Ser Gln Asn Ser Asn Thr Asp Ile Met Phe Tyr Arg Leu Ser Met Pro
    50                  55                  60

Ile Glu Cys Ala Glu Val Phe Ser Lys Thr Val Ala Gly Gly Leu Pro
65                  70                  75                  80

Gly Ala Gly Leu Phe Gly Pro Lys Asn Asp Leu Glu Asp Tyr Asp Ala
                85                  90                  95

Asp Ser Asp Phe Glu Val Leu Met Lys Thr Ala His Gly His Leu Val
            100                 105                 110

Pro Asp Arg Val Asp Lys Asp Lys Glu Ala Thr Lys Pro Glu Phe Asn
        115                 120                 125
```

```
Asn His Lys Asp Tyr Ala Gln Glu Lys Pro Ser Arg Leu Lys Gln Arg
    130                 135                 140

Phe Leu Leu Arg Arg Thr Lys Pro Asp Tyr Ser Thr Ser His Ser Ala
145                 150                 155                 160

Arg Leu Thr Glu Asp Val Leu Ala Asp Asp Arg Asp Asp Tyr Asp Phe
                165                 170                 175

Leu Met Gln Thr Ser Thr Tyr Tyr Tyr Ser Val Arg Ile Phe Pro Gly
            180                 185                 190

Gln Glu Pro Ala Asn Val Trp Val Gly Trp Ile Thr Ser Asp Phe His
        195                 200                 205

Gln Tyr Asp Thr Gly Phe Asp Leu Asp Arg Val Arg Thr Val Thr Val
    210                 215                 220

Thr Leu Gly Asp Glu Lys Gly Lys Val His Glu Ser Ile Lys Arg Ser
225                 230                 235                 240

Asn Cys Tyr Met Val Cys Ala Gly Glu Ser Met Ser Pro Gly Gln Gly
                245                 250                 255

Arg Asn Asn Asn Gly Leu Glu Ile Gly Cys Val Val Asp Ala Ala Ser
            260                 265                 270

Gly Leu Leu Thr Phe Ile Ala Asn Gly Lys Glu Leu Ser Thr Tyr Tyr
        275                 280                 285

Gln Val Glu Pro Ser Thr Lys Leu Phe Pro Ala Val Phe Ala Gln Ala
    290                 295                 300

Thr Ser Pro Asn Val Phe Gln Phe Glu Leu Gly Arg Ile Lys Asn Val
305                 310                 315                 320

Met Pro Leu Ser Ala Gly Leu Phe Lys Ser Glu His Lys Asn Pro Val
                325                 330                 335

Pro Gln Cys Pro Pro Arg Leu His Val Gln Phe Leu Ser His Val Leu
            340                 345                 350

Trp Ser Arg Met Pro Asn Gln Phe Leu Lys Val Asp Val Ser Arg Ile
        355                 360                 365

Ser Glu Arg Gln Gly Trp Leu Val Gln Cys Leu Asp Pro Leu Gln Phe
    370                 375                 380

Met Ser Leu His Ile Pro Glu Glu Asn Arg Ser Val Asp Ile
385                 390                 395
```

<210> SEQ ID NO 8
<211> LENGTH: 1194
<212> TYPE: DNA
<213> ORGANISM: Artificial Sequence
<220> FEATURE:
<223> OTHER INFORMATION: The sequence is synthetized.

<400> SEQUENCE: 8

```
aacagagaca tcaccatgtg gctgagcaag agactgcccc agttcctgca ggtgcccagc     60

aaccacgagc acatcgaggt gaccagaatc gacggcacca tcgacagcag cccctgcctg    120

aaggtgaccc agaagagctt cggcagccag aacagcaaca ccgacatcat gttctacaga    180

ctgagcatgc ccatcgagtg cgccgaggtg ttcagcaaga ccgtggccgg cggcctgccc    240

ggcgccggcc tgttcggccc caagaacgac ctggaggact acgacgccga cagcgacttc    300

gaggtgctga tgaagaccgc ccacggccac ctggtgcccg acagagtgga caaggacaag    360

gaggccacca agcccgagtt caacaaccac aaggactacg cccaggagaa gcccagcaga    420

ctgaagcaga gattcctgct gagaagaacc aagcccgact acagcaccag ccacagcgcc    480

agactgaccg aggacgtgct ggccgacgac agagacgact acgacttcct gatgcagacc    540
```

```
agcacctact actacagcgt gagaatcttc cccggccagg agcccgccaa cgtgtgggtg    600

ggctggatca ccagcgactt ccaccagtac gacaccggct tcgacctgga cagagtgaga    660

accgtgaccg tgaccctggg cgacgagaag ggcaaggtgc acgagagcat caagagaagc    720

aactgctaca tggtgtgcgc cggcgagagc atgagccccg gccagggcag aaacaacaac    780

ggcctggaga tcggctgcgt ggtggacgcc gccagcggcc tgctgacctt catcgccaac    840

ggcaaggagc tgagcaccta ctaccaggtg gagcccagca ccaagctgtt ccccgccgtg    900

ttcgcccagg ccaccagccc caacgtgttc cagttcgagc tgggcagaat caagaacgtg    960

atgcccctga gcgccggcct gttcaagagc gagcacaaga accccgtgcc ccagtgcccc   1020

cccagactgc acgtgcagtt cctgagccac gtgctgtgga gcagaatgcc caaccagttc   1080

ctgaaggtgg acgtgagcag aatcagcgag agacagggct ggctggtgca gtgcctggac   1140

cccctgcagt tcatgagcct gcacatcccc gaggagaaca gaagcgtgga catc         1194


<210> SEQ ID NO 9
<211> LENGTH: 458
<212> TYPE: PRT
<213> ORGANISM: Artificial Sequence
<220> FEATURE:
<223> OTHER INFORMATION: The sequence is synthetized.

<400> SEQUENCE: 9

Lys Phe His Tyr His Thr Leu Arg Leu Tyr Ser Ala Val Cys Ala Leu
1               5                   10                  15

Gly Asn His Arg Val Ala His Ala Leu Cys Ser His Val Asp Glu Pro
            20                  25                  30

Gln Leu Leu Tyr Ala Ile Glu Asn Lys Tyr Met Pro Gly Leu Leu Arg
        35                  40                  45

Ala Gly Tyr Tyr Asp Leu Leu Ile Asp Ile His Leu Ser Ser Tyr Ala
    50                  55                  60

Thr Ala Arg Leu Met Met Asn Asn Glu Tyr Ile Val Pro Met Thr Glu
65                  70                  75                  80

Glu Thr Lys Ser Ile Thr Leu Phe Pro Asp Glu Asn Lys Lys His Gly
                85                  90                  95

Leu Pro Gly Ile Gly Leu Ser Thr Ser Leu Arg Pro Arg Met Gln Phe
            100                 105                 110

Ser Ser Pro Ser Phe Val Ser Ile Ser Asn Glu Cys Tyr Gln Tyr Ser
        115                 120                 125

Pro Glu Phe Pro Leu Asp Ile Leu Lys Ser Lys Thr Ile Gln Met Leu
    130                 135                 140

Thr Glu Ala Val Lys Glu Gly Ser Leu His Ala Arg Asp Pro Val Gly
145                 150                 155                 160

Gly Thr Thr Glu Phe Leu Phe Val Pro Leu Ile Lys Leu Phe Tyr Thr
                165                 170                 175

Leu Leu Ile Met Gly Ile Phe His Asn Glu Asp Leu Lys His Ile Leu
            180                 185                 190

Gln Leu Ile Glu Pro Ser Val Phe Lys Glu Ala Ala Thr Pro Glu Glu
        195                 200                 205

Glu Ser Asp Thr Leu Glu Lys Glu Leu Ser Val Asp Asp Ala Lys Leu
    210                 215                 220

Gln Gly Ala Gly Glu Glu Glu Ala Lys Gly Gly Lys Arg Pro Lys Glu
225                 230                 235                 240

Gly Leu Leu Gln Met Lys Leu Pro Glu Pro Val Lys Leu Gln Met Cys
```

```
                245                 250                 255

Leu Leu Leu Gln Tyr Leu Cys Asp Cys Gln Val Arg His Arg Ile Glu
            260                 265                 270

Ala Ile Val Ala Phe Ser Asp Asp Phe Val Ala Lys Leu Gln Asp Asn
        275                 280                 285

Gln Arg Phe Arg Tyr Asn Glu Val Met Gln Ala Leu Asn Met Ser Ala
    290                 295                 300

Ala Leu Thr Ala Arg Lys Thr Lys Glu Phe Arg Ser Pro Pro Gln Glu
305                 310                 315                 320

Gln Ile Asn Met Leu Leu Asn Phe Lys Asp Asp Lys Ser Glu Cys Pro
                325                 330                 335

Cys Pro Glu Glu Ile Arg Asp Gln Leu Leu Asp Phe His Glu Asp Leu
            340                 345                 350

Met Thr His Cys Gly Ile Glu Leu Asp Glu Asp Gly Ser Leu Asp Gly
        355                 360                 365

Asn Ser Asp Leu Thr Ile Arg Gly Arg Leu Leu Ser Leu Val Glu Lys
    370                 375                 380

Val Thr Tyr Leu Lys Lys Lys Gln Ala Glu Lys Pro Val Glu Ser Asp
385                 390                 395                 400

Ser Lys Lys Ser Ser Thr Leu Gln Gln Leu Ile Ser Glu Thr Met Val
                405                 410                 415

Arg Trp Ala Gln Glu Ser Val Ile Glu Asp Pro Glu Leu Val Arg Ala
            420                 425                 430

Met Phe Val Leu Leu His Arg Gln Tyr Asp Gly Ile Gly Gly Leu Val
        435                 440                 445

Arg Ala Leu Pro Lys Thr Tyr Thr Ile Asn
    450                 455
```

<210> SEQ ID NO 10
<211> LENGTH: 1374
<212> TYPE: DNA
<213> ORGANISM: Artificial Sequence
<220> FEATURE:
<223> OTHER INFORMATION: The sequence is synthetized.

<400> SEQUENCE: 10

```
aagttccact accacaccct gagactgtac agcgccgtgt gcgccctggg caaccacaga     60

gtggcccacg ccctgtgcag ccacgtggac gagccccagc tgctgtacgc catcgagaac    120

aagtacatgc ccggcctgct gagagccggc tactacgacc tgctgatcga catccacctg    180

agcagctacg ccaccgccag actgatgatg aacaacgagt acatcgtgcc catgaccgag    240

gagaccaaga gcatcaccct gttccccgac gagaacaaga agcacggcct gcccggcatc    300

ggcctgagca ccagcctgag acccagaatg cagttcagca gccccagctt cgtgagcatc    360

agcaacgagt gctaccagta cagccccgag ttcccccctgg acatcctgaa gagcaagacc    420

atccagatgc tgaccgaggc cgtgaaggag ggcagcctgc acgccagaga ccccgtgggc    480

ggcaccaccg agttcctgtt cgtgcccctg atcaagctgt tctacaccct gctgatcatg    540

ggcatcttcc acaacgagga cctgaagcac atcctgcagc tgatcgagcc cagcgtgttc    600

aaggaggccg ccacccccga ggaggagagc gacaccctgg agaaggagct gagcgtggac    660

gacgccaagc tgcagggcgc cggcgaggag gaggccaagg gcggcaagag acccaaggag    720

ggcctgctgc agatgaagct gcccgagccc gtgaagctgc agatgtgcct gctgctgcag    780

tacctgtgcg actgccaggt gagacacaga atcgaggcca tcgtggcctt cagcgacgac    840
```

```
ttcgtggcca agctgcagga caaccagaga ttcagataca acgaggtgat gcaggccctg    900

aacatgagcg ccgccctgac cgccagaaag accaaggagt tcagaagccc cccccaggag    960

cagatcaaca tgctgctgaa cttcaaggac gacaagagcg agtgcccctg ccccgaggag   1020

atcagagacc agctgctgga cttccacgag gacctgatga cccactgcgg catcgagctg   1080

gacgaggacg gcagcctgga cggcaacagc gacctgacca tcagaggcag actgctgagc   1140

ctggtggaga aggtgaccta cctgaagaag aagcaggccg agaagcccgt ggagagcgac   1200

agcaagaaga gcagcaccct gcagcagctg atcagcgaga ccatggtgag atgggcccag   1260

gagagcgtga tcgaggaccc cgagctggtg agagccatgt tcgtgctgct gcacagacag   1320

tacgacggca tcggcggcct ggtgagagcc ctgcccaaga cctacaccat caac         1374


<210> SEQ ID NO 11
<211> LENGTH: 569
<212> TYPE: PRT
<213> ORGANISM: Artificial Sequence
<220> FEATURE:
<223> OTHER INFORMATION: The sequence is synthetized.

<400> SEQUENCE: 11

Gly Val Ser Val Glu Asp Thr Ile Asn Leu Leu Ala Ser Leu Gly Gln
1               5                   10                  15

Ile Arg Ser Leu Leu Ser Val Arg Met Gly Lys Glu Glu Glu Lys Leu
            20                  25                  30

Met Ile Arg Gly Leu Gly Asp Ile Met Asn Asn Lys Val Phe Tyr Gln
        35                  40                  45

His Pro Asn Leu Met Arg Ala Leu Gly Met His Glu Thr Val Met Glu
    50                  55                  60

Val Met Val Asn Val Leu Gly Gly Gly Glu Ser Lys Glu Ile Thr Phe
65                  70                  75                  80

Pro Lys Met Val Ala Asn Cys Cys Arg Phe Leu Cys Tyr Phe Cys Arg
                85                  90                  95

Ile Ser Arg Gln Asn Gln Lys Ala Met Phe Asp His Leu Ser Tyr Leu
            100                 105                 110

Leu Glu Asn Ser Ser Val Gly Leu Ala Ser Pro Ala Met Arg Gly Ser
        115                 120                 125

Thr Pro Leu Asp Val Ala Ala Ala Ser Val Met Asp Asn Asn Glu Leu
    130                 135                 140

Ala Leu Ala Leu Arg Glu Pro Asp Leu Glu Lys Val Val Arg Tyr Leu
145                 150                 155                 160

Ala Gly Cys Gly Leu Gln Ser Cys Gln Met Leu Val Ser Lys Gly Tyr
                165                 170                 175

Pro Asp Ile Gly Trp Asn Pro Val Glu Gly Glu Arg Tyr Leu Asp Phe
            180                 185                 190

Leu Arg Phe Ala Val Phe Cys Asn Gly Glu Ser Val Glu Glu Asn Ala
        195                 200                 205

Asn Val Val Val Arg Leu Leu Ile Arg Arg Pro Glu Cys Phe Gly Pro
    210                 215                 220

Ala Leu Arg Gly Glu Gly Gly Asn Gly Leu Leu Ala Ala Met Glu Glu
225                 230                 235                 240

Ala Ile Lys Ile Ala Glu Asp Pro Ser Arg Asp Gly Pro Ser Pro Asn
                245                 250                 255

Ser Gly Ser Ser Lys Thr Leu Asp Thr Glu Glu Glu Glu Asp Asp Thr
            260                 265                 270
```

-continued

```
Ile His Met Gly Asn Ala Ile Met Thr Phe Tyr Ser Ala Leu Ile Asp
        275                 280                 285

Leu Leu Gly Arg Cys Ala Pro Glu Met His Leu Ile His Ala Gly Lys
    290                 295                 300

Gly Glu Ala Ile Arg Ile Arg Ser Ile Leu Arg Ser Leu Ile Pro Leu
305                 310                 315                 320

Gly Asp Leu Val Gly Val Ile Ser Ile Ala Phe Gln Met Pro Thr Ile
                325                 330                 335

Ala Lys Asp Gly Asn Val Val Glu Pro Asp Met Ser Ala Gly Phe Cys
            340                 345                 350

Pro Asp His Lys Ala Ala Met Val Leu Phe Leu Asp Arg Val Tyr Gly
        355                 360                 365

Ile Glu Val Gln Asp Phe Leu Leu His Leu Leu Glu Val Gly Phe Leu
    370                 375                 380

Pro Asp Leu Arg Ala Ala Ala Ser Leu Asp Thr Ala Ala Leu Ser Ala
385                 390                 395                 400

Thr Asp Met Ala Leu Ala Leu Asn Arg Tyr Leu Cys Thr Ala Val Leu
                405                 410                 415

Pro Leu Leu Thr Arg Cys Ala Pro Leu Phe Ala Gly Thr Glu His His
            420                 425                 430

Ala Ser Leu Ile Asp Ser Leu Leu His Thr Val Tyr Arg Leu Ser Lys
        435                 440                 445

Gly Cys Ser Leu Thr Lys Ala Gln Arg Asp Ser Ile Glu Val Cys Leu
    450                 455                 460

Leu Ser Ile Cys Gly Gln Leu Arg Pro Ser Met Met Gln His Leu Leu
465                 470                 475                 480

Arg Arg Leu Val Phe Asp Val Pro Leu Leu Asn Glu His Ala Lys Met
                485                 490                 495

Pro Leu Lys Leu Leu Thr Asn His Tyr Glu Arg Cys Trp Lys Tyr Tyr
            500                 505                 510

Cys Leu Pro Gly Gly Trp Gly Asn Phe Gly Ala Ala Ser Glu Glu Glu
        515                 520                 525

Leu His Leu Ser Arg Lys Leu Phe Trp Gly Ile Phe Asp Ala Leu Ser
    530                 535                 540

Gln Lys Lys Tyr Glu Gln Glu Leu Phe Lys Leu Ala Leu Pro Cys Leu
545                 550                 555                 560

Ser Ala Val Ala Gly Ala Leu Pro Pro
                565
```

```
<210> SEQ ID NO 12
<211> LENGTH: 1707
<212> TYPE: DNA
<213> ORGANISM: Artificial Sequence
<220> FEATURE:
<223> OTHER INFORMATION: The sequence is synthetized.

<400> SEQUENCE: 12

ggcgtgagcg tggaggacac catcaacctg ctggccagcc tgggccagat cagaagcctg      60

ctgagcgtga gaatgggcaa ggaggaggag aagctgatga tcagaggcct gggcgacatc     120

atgaacaaca aggtgttcta ccagcacccc aacctgatga gagccctggg catgcacgag     180

accgtgatgg aggtgatggt gaacgtgctg ggcggcggcg agagcaagga gatcaccttc     240

cccaagatgg tggccaactg ctgcagattc ctgtgctact tctgcagaat cagcagacag     300

aaccagaagg ccatgttcga ccacctgagc tacctgctgg agaacagcag cgtgggcctg     360
```

```
gccagccccg ccatgagagg cagcaccccc ctggacgtgg ccgccgccag cgtgatggac     420

aacaacgagc tggccctggc cctgagagag cccgacctgg agaaggtggt gagatacctg     480

gccggctgcg gcctgcagag ctgccagatg ctggtgagca agggctaccc cgacatcggc     540

tggaaccccg tggagggcga gagatacctg gacttcctga gattcgccgt gttctgcaac     600

ggcgagagcg tggaggagaa cgccaacgtg gtggtgagac tgctgatcag aagacccgag     660

tgcttcggcc ccgccctgag aggcgagggc ggcaacggcc tgctggccgc catggaggag     720

gccatcaaga tcgccgagga ccccagcaga gacggcccca gccccaacag cggcagcagc     780

aagaccctgg acaccgagga ggaggaggac gacaccatcc acatgggcaa cgccatcatg     840

accttctaca gcgccctgat cgacctgctg ggcagatgcg cccccgagat gcacctgatc     900

cacgccggca agggcgaggc catcagaatc agaagcatcc tgagaagcct gatccccctg     960

ggcgacctgg tgggcgtgat cagcatcgcc ttccagatgc ccaccatcgc caaggacggc    1020

aacgtggtgg agcccgacat gagcgccggc ttctgccccg accacaaggc cgccatggtg    1080

ctgttcctgg acagagtgta cggcatcgag gtgcaggact tcctgctgca cctgctggag    1140

gtgggcttcc tgcccgacct gagagccgcc gccagcctgg acaccgccgc cctgagcgcc    1200

accgacatgg ccctggccct gaacagatac ctgtgcaccg ccgtgctgcc cctgctgacc    1260

agatgcgccc ccctgttcgc cggcaccgag caccacgcca gcctgatcga cagcctgctg    1320

cacaccgtgt acagactgag caagggctgc agcctgacca aggcccagag agacagcatc    1380

gaggtgtgcc tgctgagcat ctgcggccag ctgagaccca gcatgatgca gcacctgctg    1440

agaagactgg tgttcgacgt gcccctgctg aacgagcacg ccaagatgcc cctgaagctg    1500

ctgaccaacc actacgagag atgctggaag tactactgcc tgcccggcgg ctggggcaac    1560

ttcggcgccg ccagcgagga ggagctgcac ctgagcagaa agctgttctg ggcatcttc     1620

gacgccctga gccagaagaa gtacgagcag gagctgttca agctggccct gccctgcctg    1680

agcgccgtgg ccggcgccct gcccccc                                        1707
```

<210> SEQ ID NO 13
<211> LENGTH: 547
<212> TYPE: PRT
<213> ORGANISM: Artificial Sequence
<220> FEATURE:
<223> OTHER INFORMATION: The sequence is synthetized.

<400> SEQUENCE: 13

```
Tyr Phe Leu Ser Ala Ala Ser Arg Pro Leu Cys Ser Gly Gly His Ala
1               5                   10                  15

Ser Asn Lys Glu Lys Glu Met Val Thr Ser Leu Phe Cys Lys Leu Gly
            20                  25                  30

Val Leu Val Arg His Arg Ile Ser Leu Phe Gly Asn Asp Ala Thr Ser
        35                  40                  45

Ile Val Asn Cys Leu His Ile Leu Gly Gln Thr Leu Asp Ala Arg Thr
    50                  55                  60

Val Met Lys Thr Gly Leu Glu Ser Val Lys Ser Ala Leu Arg Ala Phe
65                  70                  75                  80

Leu Asp Asn Ala Ala Glu Asp Leu Glu Lys Thr Met Glu Asn Leu Lys
                85                  90                  95

Gln Gly Gln Phe Thr His Thr Arg Asn Gln Pro Lys Gly Val Thr Gln
            100                 105                 110

Ile Ile Asn Tyr Thr Thr Val Ala Leu Leu Pro Met Leu Ser Ser Leu
        115                 120                 125
```

-continued

```
Phe Glu His Ile Gly Gln His Gln Phe Gly Glu Asp Leu Ile Leu Glu
    130                 135                 140

Asp Val Gln Val Ser Cys Tyr Arg Ile Leu Thr Ser Leu Tyr Ala Leu
145                 150                 155                 160

Gly Thr Ser Lys Ser Ile Tyr Val Glu Arg Gln Arg Ser Ala Leu Gly
                165                 170                 175

Glu Cys Leu Ala Ala Phe Ala Gly Ala Phe Pro Val Ala Phe Leu Glu
            180                 185                 190

Thr His Leu Asp Lys His Asn Ile Tyr Ser Ile Tyr Asn Thr Lys Ser
        195                 200                 205

Ser Arg Glu Arg Ala Ala Leu Ser Leu Pro Thr Asn Val Glu Asp Val
    210                 215                 220

Cys Pro Asn Ile Pro Ser Leu Glu Lys Leu Met Glu Glu Ile Val Glu
225                 230                 235                 240

Leu Ala Glu Ser Gly Ile Arg Tyr Thr Gln Met Pro His Val Met Glu
                245                 250                 255

Val Ile Leu Pro Met Leu Cys Ser Tyr Met Ser Arg Trp Trp Glu His
            260                 265                 270

Gly Pro Glu Asn Asn Pro Glu Arg Ala Glu Met Cys Cys Thr Ala Leu
        275                 280                 285

Asn Ser Glu His Met Asn Thr Leu Leu Gly Asn Ile Leu Lys Ile Ile
    290                 295                 300

Tyr Asn Asn Leu Gly Ile Asp Glu Gly Ala Trp Met Lys Arg Leu Ala
305                 310                 315                 320

Val Phe Ser Gln Pro Ile Ile Asn Lys Val Lys Pro Gln Leu Leu Lys
                325                 330                 335

Thr His Phe Leu Pro Leu Met Glu Lys Leu Lys Lys Lys Ala Ala Thr
            340                 345                 350

Val Val Ser Glu Glu Asp His Leu Lys Ala Glu Ala Arg Gly Asp Met
        355                 360                 365

Ser Glu Ala Glu Leu Leu Ile Leu Asp Glu Phe Thr Thr Leu Ala Arg
    370                 375                 380

Asp Leu Tyr Ala Phe Tyr Pro Leu Leu Ile Arg Phe Val Asp Tyr Asn
385                 390                 395                 400

Arg Ala Lys Trp Leu Lys Glu Pro Asn Pro Glu Ala Glu Glu Leu Phe
                405                 410                 415

Arg Met Val Ala Glu Val Phe Ile Tyr Trp Ser Lys Ser His Asn Phe
            420                 425                 430

Lys Arg Glu Glu Gln Asn Phe Val Val Gln Asn Glu Ile Asn Asn Met
        435                 440                 445

Ser Phe Leu Ile Thr Asp Thr Lys Ser Lys Met Ser Lys Ala Ala Val
    450                 455                 460

Ser Asp Gln Glu Arg Lys Lys Met Lys Arg Lys Gly Asp Arg Tyr Ser
465                 470                 475                 480

Met Gln Thr Ser Leu Ile Val Ala Ala Leu Lys Arg Leu Leu Pro Ile
                485                 490                 495

Gly Leu Asn Ile Cys Ala Pro Gly Asp Gln Glu Leu Ile Ala Leu Ala
            500                 505                 510

Lys Asn Arg Phe Ser Leu Lys Asp Thr Glu Asp Glu Val Arg Asp Ile
        515                 520                 525

Ile Arg Ser Asn Ile His Leu Gln Gly Lys Leu Glu Asp Pro Ala Ile
    530                 535                 540
```

Arg Trp Gln
545

<210> SEQ ID NO 14
<211> LENGTH: 1656
<212> TYPE: DNA
<213> ORGANISM: Artificial Sequence
<220> FEATURE:
<223> OTHER INFORMATION: The sequence is synthetized.

<400> SEQUENCE: 14

```
agatacagac acgactactt cctgagcgcc gccagcagac ccctgtgcag cggcggccac     60

gccagcaaca aggagaagga gatggtgacc agcctgttct gcaagctggg cgtgctggtg    120

agacacagaa tcagcctgtt cggcaacgac gccaccagca tcgtgaactg cctgcacatc    180

ctgggccaga ccctggacgc cagaaccgtg atgaagaccg gcctggagag cgtgaagagc    240

gccctgagag ccttcctgga caacgccgcc gaggacctgg agaagaccat ggagaacctg    300

aagcagggcc agttcaccca caccagaaac cagcccaagg gcgtgaccca gatcatcaac    360

tacaccaccg tggccctgct gcccatgctg agcagcctgt tcgagcacat cggccagcac    420

cagttcggcg aggacctgat cctggaggac gtgcaggtga gctgctacag aatcctgacc    480

agcctgtacg ccctgggcac cagcaagagc atctacgtgg agagacagag aagcgccctg    540

ggcgagtgcc tggccgcctt cgccggcgcc ttccccgtgg ccttcctgga gacccacctg    600

gacaagcaca acatctacag catctacaac accaagagca gcagagagag agccgccctg    660

agcctgccca ccaacgtgga ggacgtgtgc cccaacatcc ccagcctgga gaagctgatg    720

gaggagatcg tggagctggc cgagagcggc atcagataca cccagatgcc ccacgtgatg    780

gaggtgatcc tgcccatgct gtgcagctac atgagcagat ggtgggagca cggccccgag    840

aacaaccccg agagagccga gatgtgctgc accgccctga acagcgagca catgaacacc    900

ctgctgggca acatcctgaa gatcatctac aacaacctgg gcatcgacga gggcgcctgg    960

atgaagagac tggccgtgtt cagccagccc atcatcaaca aggtgaagcc ccagctgctg   1020

aagacccact tcctgcccct gatggagaag ctgaagaaga aggccgccac cgtggtgagc   1080

gaggaggacc acctgaaggc cgaggccaga ggcgacatga gcgaggccga gctgctgatc   1140

ctggacgagt tcaccaccct ggccagagac ctgtacgcct tctacccccct gctgatcaga   1200

ttcgtggact acaacagagc caagtggctg aaggagccca accccgaggc cgaggagctg   1260

ttcagaatgg tggccgaggt gttcatctac tggagcaaga gccacaactt caagagagag   1320

gagcagaact tcgtggtgca gaacgagatc aacaacatga gcttcctgat caccgacacc   1380

aagagcaaga tgagcaaggc cgccgtgagc gaccaggaga gaaagaagat gaagagaaag   1440

ggcgacagat acagcatgca gaccagcctg atcgtggccg ccctgaagag actgctgccc   1500

atcggcctga acatctgcgc ccccggcgac caggagctga tcgccctggc caagaacaga   1560

ttcagcctga aggacaccga ggacgaggtg agagacatca tcagaagcaa catccacctg   1620

cagggcaagc tggaggaccc cgccatcaga tggcag                             1656
```

<210> SEQ ID NO 15
<211> LENGTH: 385
<212> TYPE: PRT
<213> ORGANISM: Artificial Sequence
<220> FEATURE:
<223> OTHER INFORMATION: The sequence is synthetized.

<400> SEQUENCE: 15

```
Tyr Phe Glu Asp Lys Leu Ile Glu Asp Leu Ala Lys Pro Gly Ala Glu
1               5                   10                  15

Pro Pro Glu Glu Asp Glu Gly Thr Lys Arg Val Asp Pro Leu His Gln
            20                  25                  30

Leu Ile Leu Leu Phe Ser Arg Thr Ala Leu Thr Glu Lys Cys Lys Leu
        35                  40                  45

Glu Glu Asp Phe Leu Tyr Met Ala Tyr Ala Asp Ile Met Ala Lys Ser
    50                  55                  60

Cys His Asp Glu Glu Asp Asp Asp Gly Glu Glu Glu Val Lys Ser Phe
65                  70                  75                  80

Glu Glu Lys Glu Met Glu Lys Gln Lys Leu Leu Tyr Gln Gln Ala Arg
                85                  90                  95

Leu His Asp Arg Gly Ala Ala Glu Met Val Leu Gln Thr Ile Ser Ala
            100                 105                 110

Ser Lys Gly Glu Thr Gly Pro Met Val Ala Ala Thr Leu Lys Leu Gly
        115                 120                 125

Ile Ala Ile Leu Asn Gly Gly Asn Ser Thr Val Gln Gln Lys Met Leu
    130                 135                 140

Asp Tyr Leu Lys Glu Lys Lys Asp Val Gly Phe Phe Gln Ser Leu Ala
145                 150                 155                 160

Gly Leu Met Gln Ser Cys Ser Val Leu Asp Leu Asn Ala Phe Glu Arg
                165                 170                 175

Gln Asn Lys Ala Glu Gly Leu Gly Met Val Thr Glu Glu Gly Ser Gly
            180                 185                 190

Glu Lys Val Leu Gln Asp Asp Glu Phe Thr Cys Asp Leu Phe Arg Phe
        195                 200                 205

Leu Gln Leu Leu Cys Glu Gly His Asn Ser Asp Phe Gln Asn Tyr Leu
    210                 215                 220

Arg Thr Gln Thr Gly Asn Asn Thr Thr Val Asn Ile Ile Ile Ser Thr
225                 230                 235                 240

Val Asp Tyr Leu Leu Arg Val Gln Glu Ser Ile Ser Asp Phe Tyr Trp
                245                 250                 255

Tyr Tyr Ser Gly Lys Asp Val Ile Asp Glu Gln Gly Gln Arg Asn Phe
            260                 265                 270

Ser Lys Ala Ile Gln Val Ala Lys Gln Val Phe Asn Thr Leu Thr Glu
        275                 280                 285

Tyr Ile Gln Gly Pro Cys Thr Gly Asn Gln Gln Ser Leu Ala His Ser
    290                 295                 300

Arg Leu Trp Asp Ala Val Val Gly Phe Leu His Val Phe Ala His Met
305                 310                 315                 320

Gln Met Lys Leu Ser Gln Asp Ser Ser Gln Ile Glu Leu Leu Lys Glu
                325                 330                 335

Leu Met Asp Leu Gln Lys Asp Met Val Val Met Leu Leu Ser Met Leu
            340                 345                 350

Glu Gly Asn Val Val Asn Gly Thr Ile Gly Lys Gln Met Val Asp Met
        355                 360                 365

Leu Val Glu Ser Ser Asn Asn Val Glu Met Ile Leu Lys Phe Phe Asp
    370                 375                 380

Met
385
```

<210> SEQ ID NO 16
<211> LENGTH: 1155
<212> TYPE: DNA

<213> ORGANISM: Artificial Sequence
<220> FEATURE:
<223> OTHER INFORMATION: The sequence is synthetized.

<400> SEQUENCE: 16

```
tacttcgagg acaagctgat cgaggacctg gccaagcccg gcgccgagcc ccccgaggag     60

gacgagggca ccaagagagt ggaccccctg caccagctga tcctgctgtt cagcagaacc    120

gccctgaccg agaagtgcaa gctggaggag gacttcctgt acatggccta cgccgacatc    180

atggccaaga gctgccacga cgaggaggac gacgacggcg aggaggaggt gaagagcttc    240

gaggagaagg agatggagaa gcagaagctg ctgtaccagc aggccagact gcacgacaga    300

ggcgccgccg agatggtgct gcagaccatc agcgccagca agggcgagac cggccccatg    360

gtggccgcca ccctgaagct gggcatcgcc atcctgaacg gcggcaacag caccgtgcag    420

cagaagatgc tggactacct gaaggagaag aaggacgtgg gcttcttcca gagcctggcc    480

ggcctgatgc agagctgcag cgtgctggac ctgaacgcct tcgagagaca gaacaaggcc    540

gagggcctgg gcatggtgac cgaggagggc agcggcgaga aggtgctgca ggacgacgag    600

ttcacctgcg acctgttcag attcctgcag ctgctgtgcg agggccacaa cagcgacttc    660

cagaactacc tgagaaccca gaccggcaac aacaccaccg tgaacatcat catcagcacc    720

gtggactacc tgctgagagt gcaggagagc atcagcgact tctactggta ctacagcggc    780

aaggacgtga tcgacgagca gggccagaga aacttcagca aggccatcca ggtggccaag    840

caggtgttca acaccctgac cgagtacatc cagggcccct gcaccggcaa ccagcagagc    900

ctggcccaca gcagactgtg ggacgccgtg gtgggcttcc tgcacgtgtt cgcccacatg    960

cagatgaagc tgagccagga cagcagccag atcgagctgc tgaaggagct gatggacctg   1020

cagaaggaca tggtggtgat gctgctgagc atgctggagg gcaacgtggt gaacggcacc   1080

atcggcaagc agatggtgga catgctggtg gagagcagca acaacgtgga gatgatcctg   1140

aagttcttcg acatg                                                    1155
```

<210> SEQ ID NO 17
<211> LENGTH: 61
<212> TYPE: PRT
<213> ORGANISM: Artificial Sequence
<220> FEATURE:
<223> OTHER INFORMATION: The sequence is synthetized.

<400> SEQUENCE: 17

```
Leu Thr Ser Ser Asp Thr Phe Lys Glu Tyr Asp Pro Asp Gly Lys Gly
1               5                   10                  15

Val Ile Ser Lys Arg Asp Phe His Lys Ala Met Glu Ser His Lys His
            20                  25                  30

Tyr Thr Gln Ser Glu Thr Glu Phe Leu Leu Ser Cys Ala Glu Thr Asp
        35                  40                  45

Glu Asn Glu Thr Leu Asp Tyr Glu Glu Phe Val Lys Arg
    50                  55                  60
```

<210> SEQ ID NO 18
<211> LENGTH: 183
<212> TYPE: DNA
<213> ORGANISM: Artificial Sequence
<220> FEATURE:
<223> OTHER INFORMATION: The sequence is synthetized.

<400> SEQUENCE: 18

```
ctgaccagca gcgacacctt caaggagtac gaccccgacg gcaagggcgt gatcagcaag     60
```

```
agagacttcc acaaggccat ggagagccac aagcactaca cccagagcga gaccgagttc    120

ctgctgagct gcgccgagac cgacgagaac gagaccctgg actacgagga gttcgtgaag    180

aga                                                                  183


<210> SEQ ID NO 19
<211> LENGTH: 117
<212> TYPE: PRT
<213> ORGANISM: Artificial Sequence
<220> FEATURE:
<223> OTHER INFORMATION: The sequence is synthetized.

<400> SEQUENCE: 19

Pro Ala Lys Asp Ile Gly Phe Asn Val Ala Val Leu Leu Thr Asn Leu
1               5                   10                  15

Ser Glu His Met Pro Asn Asp Thr Arg Leu Gln Thr Phe Leu Glu Leu
            20                  25                  30

Ala Glu Ser Val Leu Asn Tyr Phe Gln Pro Phe Leu Gly Arg Ile Glu
        35                  40                  45

Ile Met Gly Ser Ala Lys Arg Ile Glu Arg Val Tyr Phe Glu Ile Ser
    50                  55                  60

Glu Ser Ser Arg Thr Gln Trp Glu Lys Pro Gln Val Lys Glu Ser Lys
65                  70                  75                  80

Arg Gln Phe Ile Phe Asp Val Val Asn Glu Gly Gly Glu Lys Glu Lys
                85                  90                  95

Met Glu Leu Phe Val Asn Phe Cys Glu Asp Thr Ile Phe Glu Met Gln
            100                 105                 110

Leu Ala Ala Gln Ile
        115


<210> SEQ ID NO 20
<211> LENGTH: 351
<212> TYPE: DNA
<213> ORGANISM: Artificial Sequence
<220> FEATURE:
<223> OTHER INFORMATION: The sequence is synthetized.

<400> SEQUENCE: 20

cccgccaagg acatcggctt caacgtggcc gtgctgctga ccaacctgag cgagcacatg     60

cccaacgaca ccagactgca gaccttcctg gagctggccg agagcgtgct gaactacttc    120

cagcccttcc tgggcagaat cgagatcatg ggcagcgcca agagaatcga gagagtgtac    180

ttcgagatca gcgagagcag cagaacccag tgggagaagc cccaggtgaa ggagagcaag    240

agacagttca tcttcgacgt ggtgaacgag ggcggcgaga aggagaagat ggagctgttc    300

gtgaacttct gcgaggacac catcttcgag atgcagctgg ccgcccagat c             351


<210> SEQ ID NO 21
<211> LENGTH: 207
<212> TYPE: PRT
<213> ORGANISM: Artificial Sequence
<220> FEATURE:
<223> OTHER INFORMATION: The sequence is synthetized.

<400> SEQUENCE: 21

Asn Phe Asn Pro Gln Pro Val Asp Thr Ser Asn Ile Thr Ile Pro Glu
1               5                   10                  15

Lys Leu Glu Tyr Phe Ile Asn Lys Tyr Ala Glu His Ser His Asp Lys
            20                  25                  30
```

```
Trp Ser Met Asp Lys Leu Ala Asn Gly Trp Ile Tyr Gly Glu Ile Tyr
        35                  40                  45

Ser Asp Ser Ser Lys Val Gln Pro Leu Met Lys Pro Tyr Lys Leu Leu
    50                  55                  60

Ser Glu Lys Glu Lys Glu Ile Tyr Arg Trp Pro Ile Lys Glu Ser Leu
65                  70                  75                  80

Lys Thr Met Leu Ala Trp Gly Trp Arg Ile Glu Arg Thr Arg Glu Gly
                85                  90                  95

Asp Ser Met Ala Leu Tyr Asn Arg Thr Arg Arg Ile Ser Gln Thr Ser
            100                 105                 110

Gln Val Ser Val Asp Ala Ala His Gly Tyr Ser Pro Arg Ala Ile Asp
        115                 120                 125

Met Ser Asn Val Thr Leu Ser Arg Asp Leu His Ala Met Ala Glu Met
    130                 135                 140

Met Ala Glu Asn Tyr His Asn Ile Trp Ala Lys Lys Lys Lys Met Glu
145                 150                 155                 160

Leu Glu Ser Lys Gly Gly Gly Asn His Pro Leu Leu Val Pro Tyr Asp
                165                 170                 175

Thr Leu Thr Ala Lys Glu Lys Ala Lys Asp Arg Glu Lys Ala Gln Asp
            180                 185                 190

Ile Leu Lys Phe Leu Gln Ile Asn Gly Tyr Ala Val Ser Arg Gly
        195                 200                 205


<210> SEQ ID NO 22
<211> LENGTH: 621
<212> TYPE: DNA
<213> ORGANISM: Artificial Sequence
<220> FEATURE:
<223> OTHER INFORMATION: The sequence is synthetized.

<400> SEQUENCE: 22

aacttcaacc cccagcccgt ggacaccagc aacatcacca tccccgagaa gctggagtac      60

ttcatcaaca agtacgccga gcacagccac gacaagtgga gcatggacaa gctggccaac     120

ggctggatct acggcgagat ctacagcgac agcagcaagg tgcagcccct gatgaagccc     180

tacaagctgc tgagcgagaa ggagaaggag atctacagat ggcccatcaa ggagagcctg     240

aagaccatgc tggcctgggg ctggagaatc gagagaacca gagagggcga cagcatggcc     300

ctgtacaaca gaaccagaag aatcagccag accagccagg tgagcgtgga cgccgcccac     360

ggctacagcc ccagagccat cgacatgagc aacgtgaccc tgagcagaga cctgcacgcc     420

atggccgaga tgatggccga gaactaccac aacatctggg ccaagaagaa gaagatggag     480

ctggagagca agggcggcgg caaccacccc ctgctggtgc cctacgacac cctgaccgcc     540

aaggagaagg ccaaggacag agagaaggcc caggacatcc tgaagttcct gcagatcaac     600

ggctacgccg tgagcagagg c                                               621


<210> SEQ ID NO 23
<211> LENGTH: 156
<212> TYPE: PRT
<213> ORGANISM: Artificial Sequence
<220> FEATURE:
<223> OTHER INFORMATION: The sequence is synthetized.

<400> SEQUENCE: 23

Gln Pro Val Asp Thr Ser Asn Ile Thr Ile Pro Glu Lys Leu Glu Tyr
1               5                   10                  15

Phe Ile Asn Lys Tyr Ala Glu His Ser His Asp Lys Trp Ser Met Asp
```

```
            20                  25                  30

Lys Leu Ala Asn Gly Trp Ile Tyr Gly Glu Ile Tyr Ser Asp Ser Ser
        35                  40                  45

Lys Val Gln Pro Leu Met Lys Pro Tyr Lys Leu Leu Ser Glu Lys Glu
    50                  55                  60

Lys Glu Ile Tyr Arg Trp Pro Ile Lys Glu Ser Leu Lys Thr Met Leu
65                  70                  75                  80

Ala Trp Gly Trp Arg Ile Glu Arg Thr Arg Glu Gly Asp Ser Met Ala
                85                  90                  95

Leu Tyr Asn Arg Thr Arg Arg Ile Ser Gln Thr Ser Gln Val Ser Val
            100                 105                 110

Asp Ala Ala His Gly Tyr Ser Pro Arg Ala Ile Asp Met Ser Asn Val
        115                 120                 125

Thr Leu Ser Arg Asp Leu His Ala Met Ala Glu Met Met Ala Glu Asn
    130                 135                 140

Tyr His Asn Ile Trp Ala Lys Lys Lys Lys Met Glu
145                 150                 155


<210> SEQ ID NO 24
<211> LENGTH: 468
<212> TYPE: DNA
<213> ORGANISM: Artificial Sequence
<220> FEATURE:
<223> OTHER INFORMATION: The sequence is synthetized.

<400> SEQUENCE: 24

cagcccgtgg acaccagcaa catcaccatc cccgagaagc tggagtactt catcaacaag     60

tacgccgagc acagccacga caagtggagc atggacaagc tggccaacgg ctggatctac    120

ggcgagatct acagcgacag cagcaaggtg cagcccctga tgaagcccta caagctgctg    180

agcgagaagg agaaggagat ctacagatgg cccatcaagg agagcctgaa gaccatgctg    240

gcctggggct ggagaatcga gagaaccaga gagggcgaca gcatggccct gtacaacaga    300

accagaagaa tcagccagac cagccaggtg agcgtggacg ccgcccacgg ctacagcccc    360

agagccatcg acatgagcaa cgtgaccctg agcagagacc tgcacgccat ggccgagatg    420

atggccgaga actaccacaa catctgggcc aagaagaaga agatggag                 468


<210> SEQ ID NO 25
<211> LENGTH: 69
<212> TYPE: PRT
<213> ORGANISM: Artificial Sequence
<220> FEATURE:
<223> OTHER INFORMATION: The sequence is synthetized.

<400> SEQUENCE: 25

Ile Tyr Arg Trp Pro Ile Lys Glu Ser Leu Lys Thr Met Leu Ala Trp
1               5                   10                  15

Gly Trp Arg Ile Glu Arg Thr Arg Glu Gly Asp Ser Met Ala Leu Tyr
            20                  25                  30

Asn Arg Thr Arg Arg Ile Ser Gln Thr Ser Gln Val Ser Val Asp Ala
        35                  40                  45

Ala His Gly Tyr Ser Pro Arg Ala Ile Asp Met Ser Asn Val Thr Leu
    50                  55                  60

Ser Arg Asp Leu His
65


<210> SEQ ID NO 26
```

<211> LENGTH: 207
<212> TYPE: DNA
<213> ORGANISM: Artificial Sequence
<220> FEATURE:
<223> OTHER INFORMATION: The sequence is synthetized.

<400> SEQUENCE: 26
atctacagat ggcccatcaa ggagagcctg aagaccatgc tggcctgggg ctggagaatc 60
gagagaacca gagagggcga cagcatggcc ctgtacaaca gaaccagaag aatcagccag 120
accagccagg tgagcgtgga cgccgcccac ggctacagcc ccagagccat cgacatgagc 180
aacgtgaccc tgagcagaga cctgcac 207

<210> SEQ ID NO 27
<211> LENGTH: 17
<212> TYPE: PRT
<213> ORGANISM: Artificial Sequence
<220> FEATURE:
<223> OTHER INFORMATION: The sequence is synthetized.

<400> SEQUENCE: 27

Thr Arg Arg Ile Ser Gln Thr Ser Gln Val Ser Val Asp Ala Ala His
1 5 10 15

Gly

<210> SEQ ID NO 28
<211> LENGTH: 51
<212> TYPE: DNA
<213> ORGANISM: Artificial Sequence
<220> FEATURE:
<223> OTHER INFORMATION: The sequence is synthetized.

<400> SEQUENCE: 28
accagaagaa tcagccagac cagccaggtg agcgtggacg ccgcccacgg c 51

<210> SEQ ID NO 29
<211> LENGTH: 206
<212> TYPE: PRT
<213> ORGANISM: Artificial Sequence
<220> FEATURE:
<223> OTHER INFORMATION: The sequence is synthetized.

<400> SEQUENCE: 29

Asn Phe Asn Pro Gln Pro Val Asp Thr Ser Asn Ile Thr Ile Pro Glu
1 5 10 15

Lys Leu Glu Tyr Phe Ile Asn Lys Tyr Ala Glu His Ser His Asp Lys
20 25 30

Trp Ser Met Asp Lys Leu Ala Asn Gly Trp Ile Tyr Gly Glu Ile Tyr
35 40 45

Ser Asp Ser Ser Lys Ile Gln Pro Leu Met Lys Pro Tyr Lys Leu Leu
50 55 60

Ser Glu Lys Glu Lys Glu Ile Tyr Arg Trp Pro Ile Lys Glu Ser Leu
65 70 75 80

Lys Thr Met Leu Ala Trp Gly Trp Arg Ile Glu Arg Thr Arg Glu Gly
85 90 95

Asp Ser Met Ala Leu Tyr Asn Arg Thr Arg Arg Ile Ser Gln Thr Ser
100 105 110

Gln Val Ser Ile Asp Ala Ala His Gly Tyr Ser Pro Arg Ala Ile Asp
115 120 125

Met Ser Asn Val Thr Leu Ser Arg Asp Leu His Ala Met Ala Glu Met
130 135 140

-continued

```
Met Ala Glu Asn Tyr His Asn Ile Trp Ala Lys Lys Lys Lys Leu Glu
145                 150                 155                 160

Leu Glu Ser Lys Gly Gly Gly Asn His Pro Leu Leu Val Pro Tyr Asp
                165                 170                 175

Thr Leu Thr Ala Lys Glu Lys Ala Lys Asp Arg Glu Lys Ala Gln Asp
            180                 185                 190

Ile Leu Lys Phe Leu Gln Ile Asn Gly Tyr Ala Val Ser Arg
        195                 200                 205


<210> SEQ ID NO 30
<211> LENGTH: 618
<212> TYPE: DNA
<213> ORGANISM: Artificial Sequence
<220> FEATURE:
<223> OTHER INFORMATION: The sequence is synthetized.

<400> SEQUENCE: 30

aacttcaacc cccagcccgt ggacaccagc aacatcacca tccccgagaa gctggagtac     60

ttcatcaaca agtacgccga gcacagccac gacaagtgga gcatggacaa gctggccaac    120

ggctggatct acggcgagat ctacagcgac agcagcaaga tccagcccct gatgaagccc    180

tacaagctgc tgagcgagaa ggagaaggag atctacagat ggcccatcaa ggagagcctg    240

aagaccatgc tggcctgggg ctggagaatc gagagaacca gagagggcga cagcatggcc    300

ctgtacaaca gaaccagaag aatcagccag accagccagg tgagcatcga cgccgcccac    360

ggctacagcc ccagagccat cgacatgagc aacgtgaccc tgagcagaga cctgcacgcc    420

atggccgaga tgatggccga gaactaccac aacatctggg ccaagaagaa gaagctggag    480

ctggagagca agggcggcgg caaccacccc ctgctggtgc cctacgacac cctgaccgcc    540

aaggagaagg ccaaggacag agagaaggcc caggacatcc tgaagttcct gcagatcaac    600

ggctacgccg tgagcaga                                                  618
```